US010278597B2

(12) United States Patent
Kuno

(10) Patent No.: US 10,278,597 B2
(45) Date of Patent: May 7, 2019

(54) PULSE DATA DETECTING APPARATUS, PULSE DATA DETECTING METHOD, AND STORAGE MEDIUM HAVING PULSE DATA DETECTION PROGRAM RECORDED THEREON

(71) Applicant: CASIO COMPUTER CO., LTD., Shibuya-ku, Tokyo (JP)

(72) Inventor: Toshiya Kuno, Hamura (JP)

(73) Assignee: CASIO COMPUTER CO., LTD., Tokyo (JP)

(*) Notice: Subject to any disclaimer, the term of this patent is extended or adjusted under 35 U.S.C. 154(b) by 1025 days.

(21) Appl. No.: 14/028,301

(22) Filed: Sep. 16, 2013

(65) Prior Publication Data
US 2014/0081161 A1  Mar. 20, 2014

(30) Foreign Application Priority Data

Sep. 18, 2012 (JP) ................ 2012-204422
Jul. 5, 2013 (JP) ................ 2013-141223

(51) Int. Cl.
*A61B 5/00* (2006.01)
*A61B 5/021* (2006.01)
(Continued)

(52) U.S. Cl.
CPC .......... *A61B 5/025* (2013.01); *A61B 5/02422* (2013.01); *A61B 5/02438* (2013.01);
(Continued)

(58) Field of Classification Search
CPC ....... A61B 5/021; A61B 5/022; A61B 5/4854; A61B 5/6824; A61B 5/02108;
(Continued)

(56) References Cited

U.S. PATENT DOCUMENTS 3,348,534 A * 10/1967 Marx .................... A61B 5/022
600/492
6,198,951 B1   3/2001 Kosuda et al.
(Continued)

FOREIGN PATENT DOCUMENTS

CN    1320411 A    11/2001
CN    1517059 A     8/2004
(Continued)

OTHER PUBLICATIONS

Chinese Office Action (and English translation thereof) dated Dec. 9, 2015, issued in counterpart Chinese Application No. 2013104290041.7.

(Continued)

*Primary Examiner* — Christian Jang
*Assistant Examiner* — Karen E Toth
(74) *Attorney, Agent, or Firm* — Holtz, Holtz & Volek PC

(57) ABSTRACT

A pulse data detecting apparatus, pulse data detecting method, and pulse data detection program are provided capable of suppressing an influence of the condition of the body surface to be measured and obtaining an appropriate measurement result under a wide range of conditions. In the present invention, a blood-flow-suppressing-projection protrusion-control mechanism section causes a blood-flow-suppressing projection to protrude to press or compress the body surface to suppress a blood flow on a downstream side, thereby increasing a blood pressure of a measurement region at the time of measurement. A light-receiving element receives reflected light of light applied from a light-emitting element to a skin surface, and outputs an electrical signal. Increasing the blood pressure of the measurement region enables to obtain an output signal at a sufficient output level from the light-receiving element. A CPU calculates a pulse (Continued)

rate based on the output signal from the light-receiving element.

18 Claims, 17 Drawing Sheets

(51) Int. Cl.
A61B 5/022 (2006.01)
A61B 5/024 (2006.01)
A61B 5/025 (2006.01)

(52) U.S. Cl.
CPC .............. *A61B 5/683* (2013.01); *A61B 5/021* (2013.01); *A61B 5/022* (2013.01); *A61B 5/02108* (2013.01); *A61B 5/4854* (2013.01)

(58) Field of Classification Search
CPC . A61B 5/02241; A61B 5/024; A61B 5/02427; A61B 5/0255; A61B 5/02
See application file for complete search history.

(56) References Cited

U.S. PATENT DOCUMENTS

| | | | |
|---|---|---|---|
| 6,400,971 B1* | 6/2002 | Finarov | A61B 5/02241 600/310 |
| 6,544,188 B1* | 4/2003 | Chesney | A61B 5/022 600/500 |
| 7,144,373 B2 | 12/2006 | Sato et al. | |
| 7,306,563 B2* | 12/2007 | Huang | A61B 5/021 600/485 |
| 2002/0169381 A1* | 11/2002 | Asada | A61B 5/14552 600/485 |
| 2004/0193061 A1 | 9/2004 | Sato et al. | |
| 2006/0206031 A1* | 9/2006 | Hasegawa | A61B 5/02116 600/490 |
| 2007/0088225 A1 | 4/2007 | Tanaka et al. | |
| 2010/0234743 A1* | 9/2010 | Kohyama | A61B 5/02233 600/499 |
| 2011/0282219 A1* | 11/2011 | Parzy | A61B 5/02141 600/490 |

FOREIGN PATENT DOCUMENTS

| | | |
|---|---|---|
| CN | 102462493 A | 5/2012 |
| JP | 2007-105338 A | 4/2007 |
| JP | 2008-054890 A | 3/2008 |
| JP | 2008048987 A | 3/2008 |
| JP | 2009006070 A | 1/2009 |
| JP | 2009-231577 A | 10/2009 |
| JP | 4848732 B2 | 12/2011 |
| WO | 9912469 A1 | 3/1999 |
| WO | 2011162000 A1 | 12/2011 |

OTHER PUBLICATIONS

Chinese Office Action (and English translation thereof) dated Apr. 17, 2015, issued in counterpart Chinese Application No. 201310429004.7.

Japanese Office Action (and English translation thereof) dated Apr. 3, 2017 issued in counterpart Japanese Application No. 2013-141223.

Japanese Office Action (and English language translation thereof) dated Oct. 30, 2018 issued in counterpart Japanese Application No. 2017-228877.

* cited by examiner

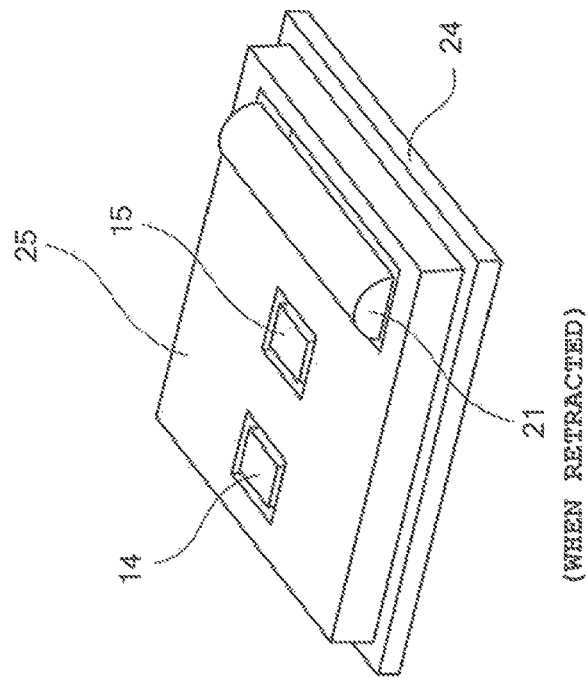
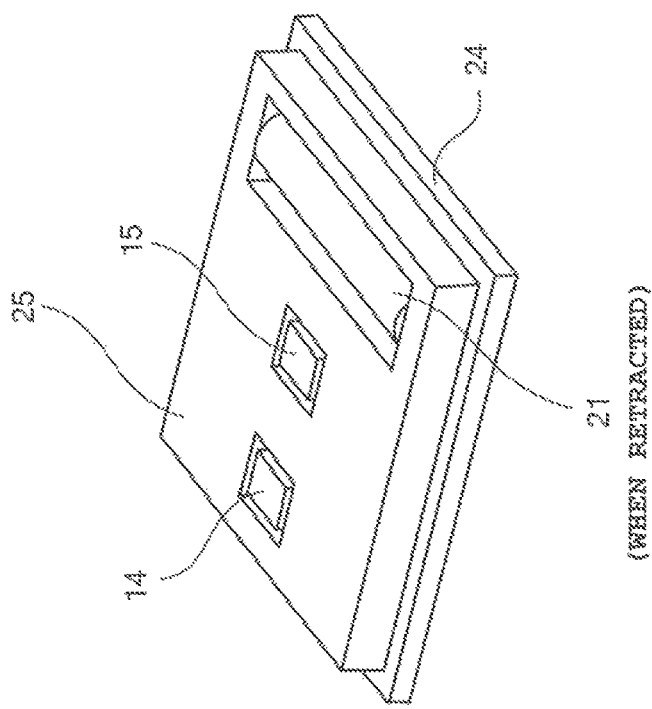

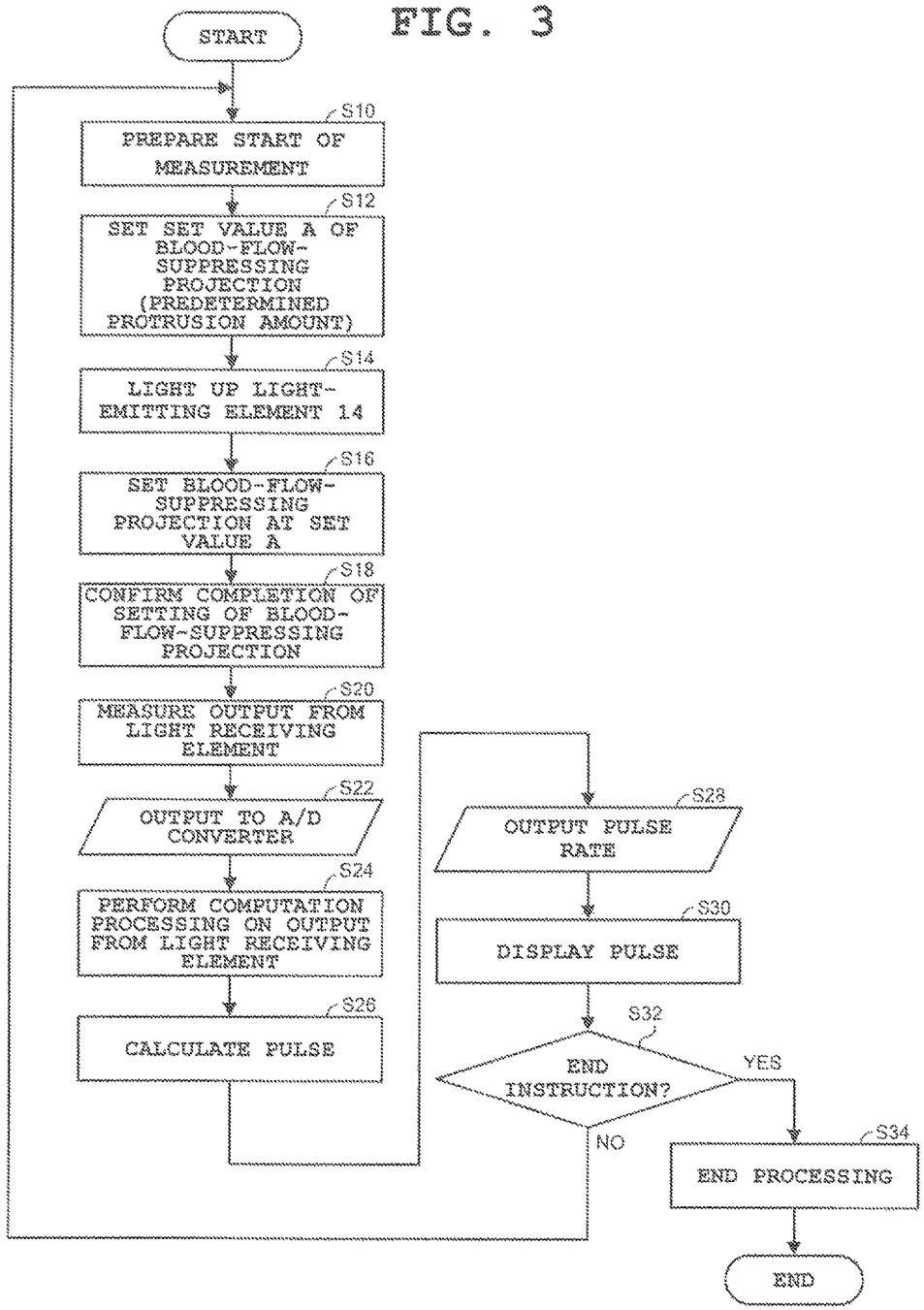

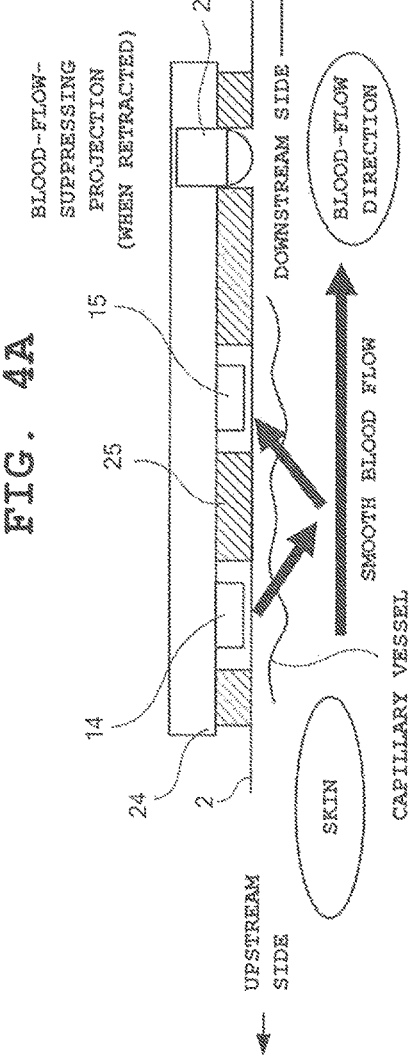
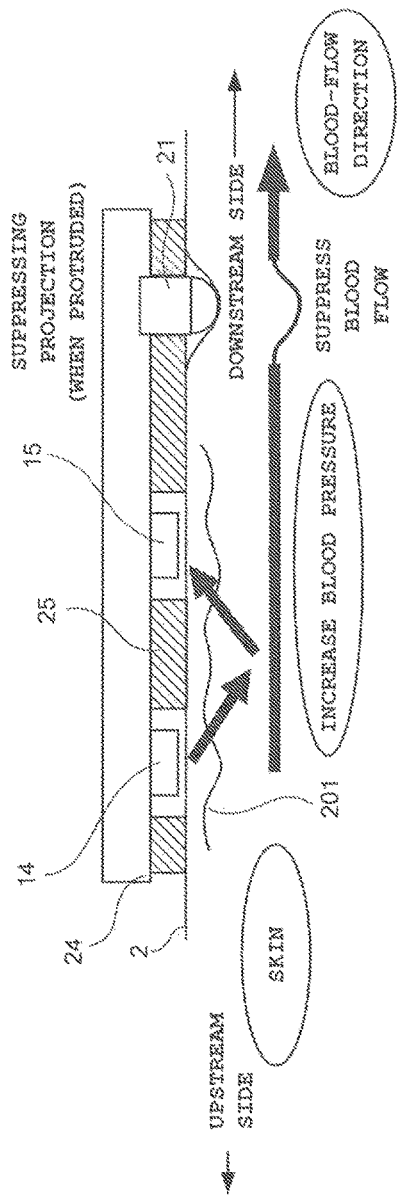

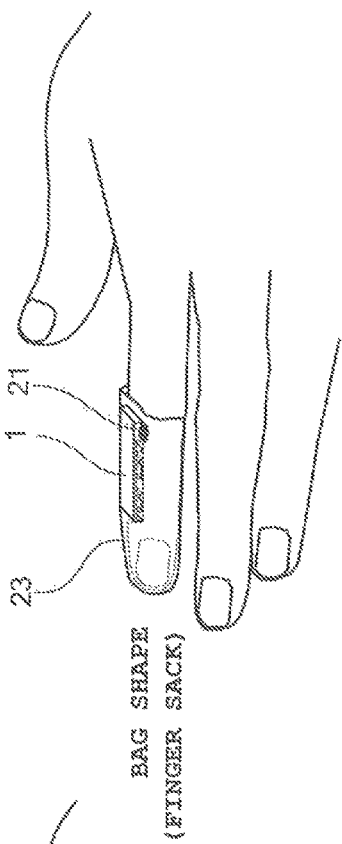
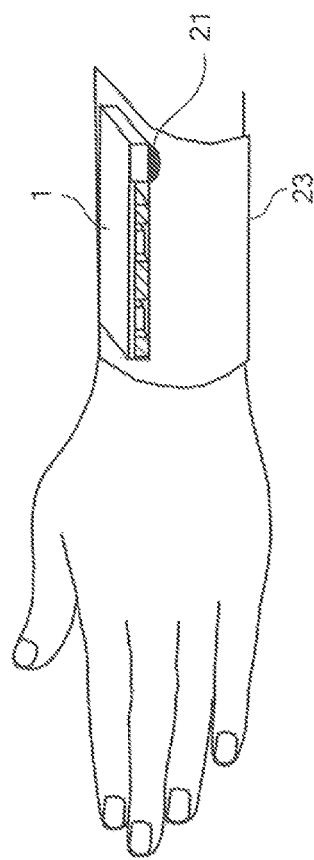
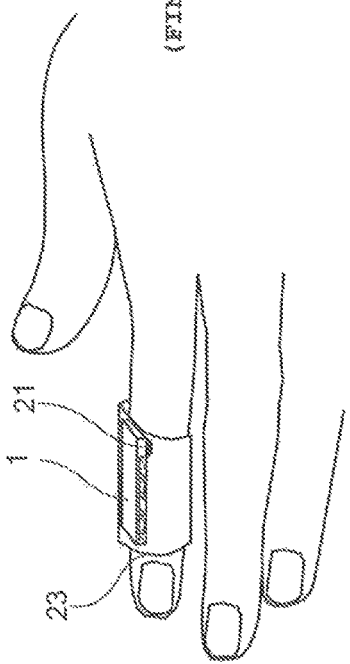

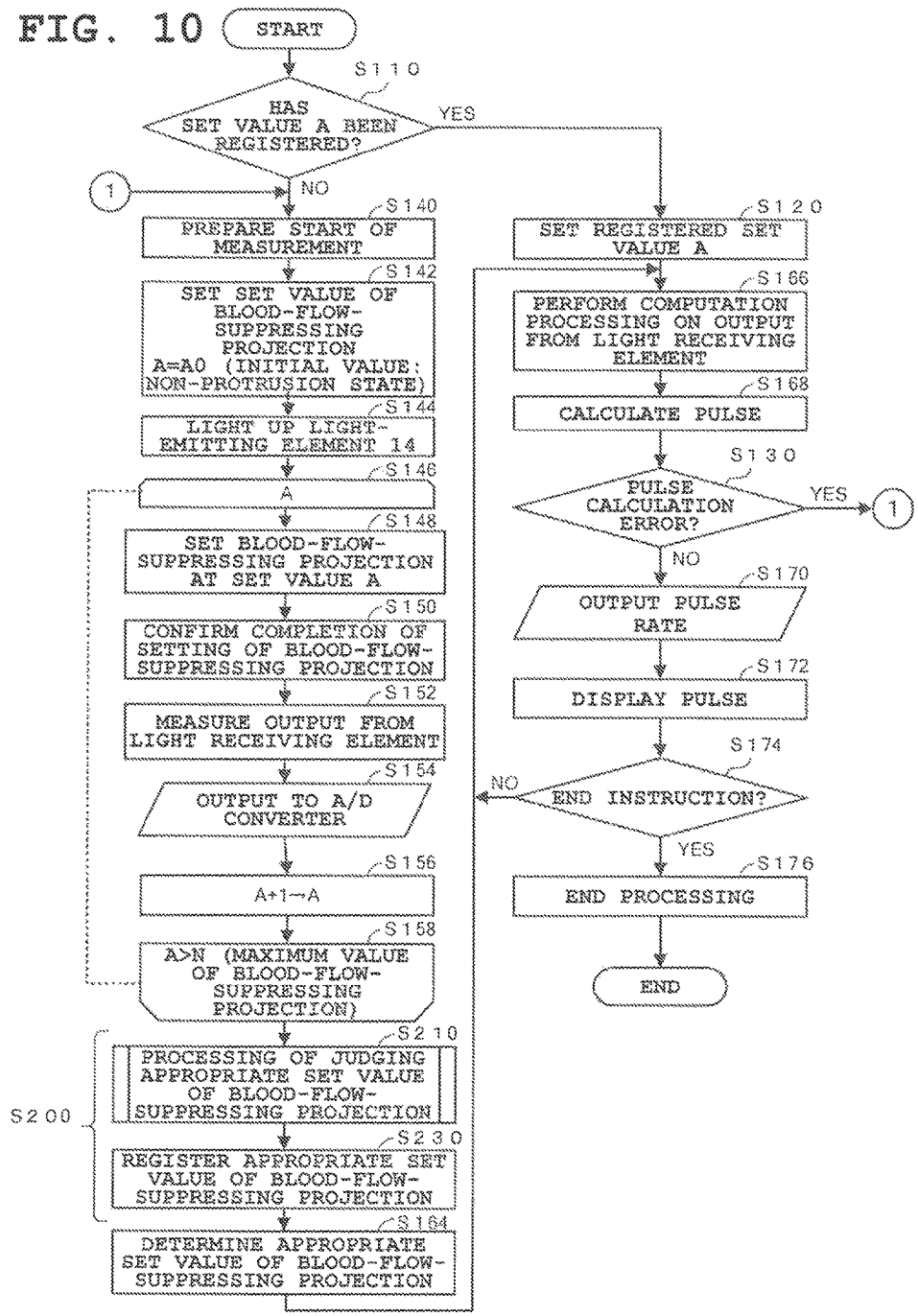

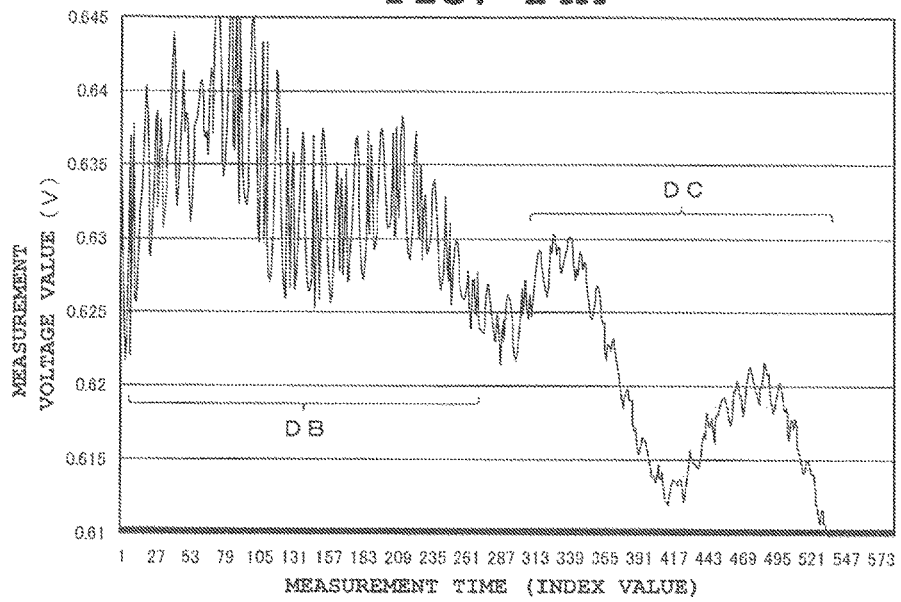
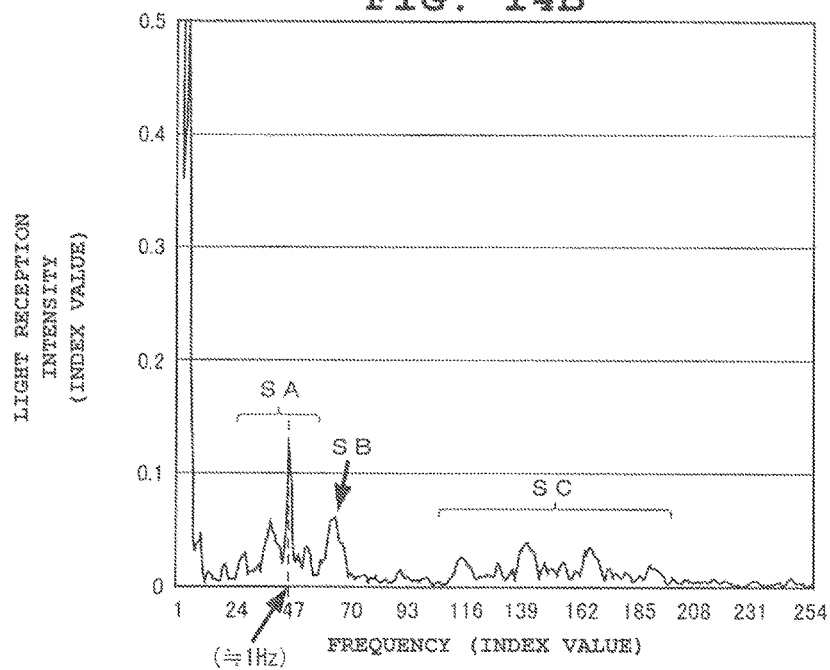

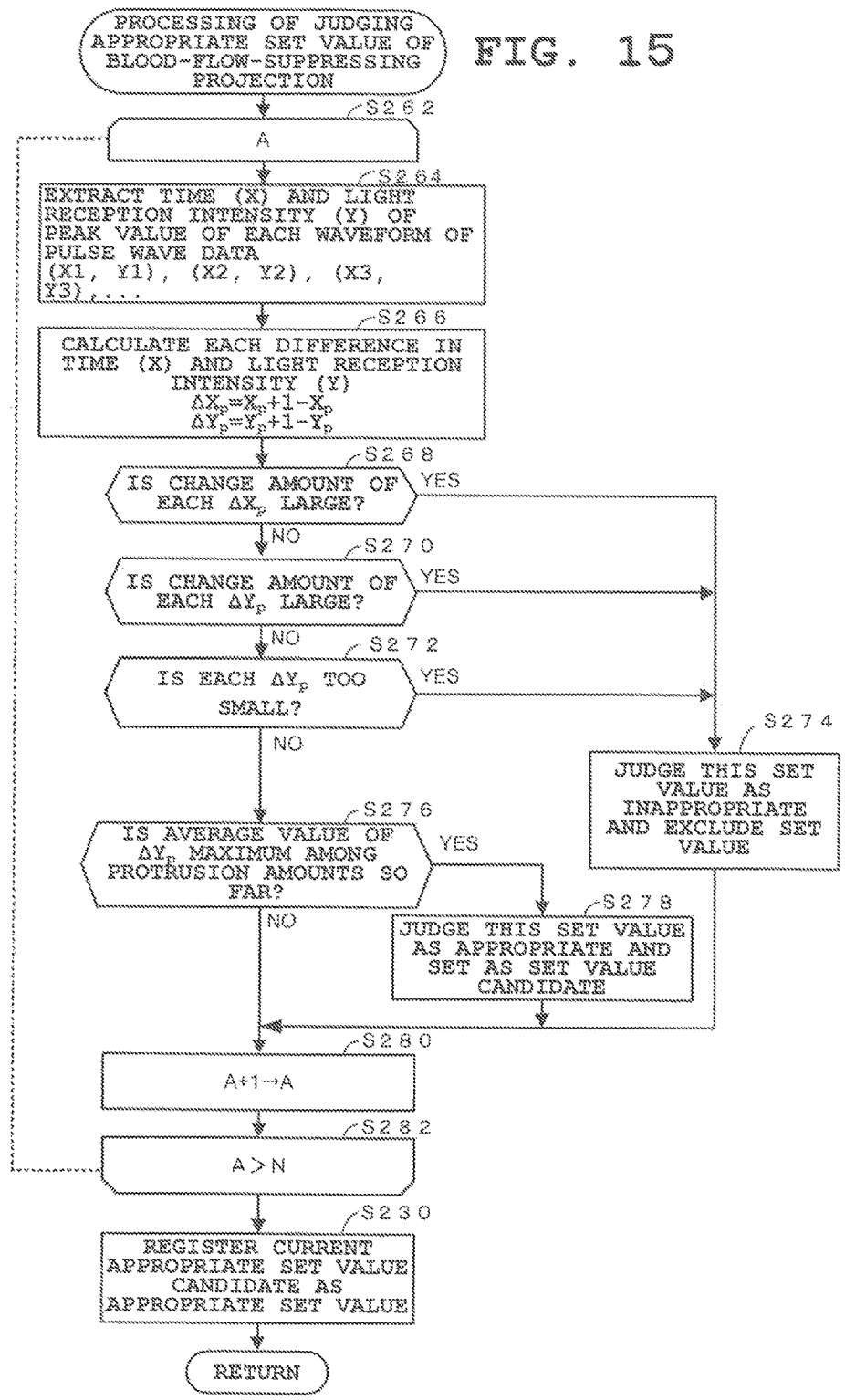

PRIOR ART

PRIOR ART

PULSE DATA DETECTING APPARATUS, PULSE DATA DETECTING METHOD, AND STORAGE MEDIUM HAVING PULSE DATA DETECTION PROGRAM RECORDED THEREON

CROSS-REFERENCE TO RELATED APPLICATIONS

This application is based upon and claims the benefit of priority from the prior Japanese Patent Application No. 2012-204422, filed Sep. 18, 2012, and No. 2013-141223, filed Jul. 5, 2013, the entire contents of which are incorporated herein by reference.

BACKGROUND OF THE INVENTION

1. Field of the Invention

The present invention relates to a pulse data detecting apparatus mounted on a human body to measure pulse data, pulse data detecting method, and the like.

2. Description of the Related Art

Conventionally, various types have been available for apparatuses of measuring pulse of a human body. By way of example, a method of obtaining an electrical signal flowing at both ends of the trunk across the heart (an application of an electrocardiogram) and a method of measuring the sound of heartbeat together with measuring a blood pressure are known. Also, based on using the fact that the light absorption amount changes with change in concentration (density) of hemoglobin flowing through capillary vessels distributed over the body surface, a (so-called optical) method of using the principle that the light amount of reflected light changes with heartbeat is also known as another example of the method for measuring pulses. In this method, the human skin is irradiated with light such as visible light (green or red) or near-infrared light and a change in body-surface reflected light or a change in absorption light amount of hemoglobin by body transmission light is measured.

Among these various types of measuring devices, a scheme called an optical type has been disclosed in, for example, Japanese Patent Application Laid-Oben (Kokai) Publication No, 2007-105338 and Japanese Patent Application Laid-Open (Kokai) Publication No. 2009-231577, describing a technology of measuring pulse data based on a detection signal obtained by receiving, at a light-receiving element, reflected light of light applied from a light-emitting element to the body surface.

FIG. 16 is a perspective view of an example of external appearance, schematically depicting the structure of a pulse data detecting apparatus 100 described in Japanese Patent Application Laid-Open (Kokai) Publication No. 2009-231577. In FIG. 16, on a circuit board 101 having various circuits mounted thereon, a light-emitting element 102 and a light-receiving element 103 are arranged with a predetermined space apart from each other. Around the light-emitting element 102 and the light-receiving element 103, a light-shielding block 104 is arranged. The light-shielding block 104 is formed higher than the light-emitting element 102 and the light-receiving element 103.

FIG. 17 is a cross-sectional view of the state of the pulse data detecting apparatus 100 depicted in FIG. 16 at the time of pulse data detection. The pulse data detecting apparatus 100 is pressed onto the skin surface of the arm or the like of a test subject so as to face the light-emitting element 102 and the light-receiving element 103 and the skin surface each other, and is fixed as required. Here, the light-shielding block 104 makes close contact with a skin surface 200. As a result, light applied from the light-emitting element 102 is prevented from being directly received by the light-receiving element 103, and reflected light from the inside of the skin reaches the light-receiving element 103. The pulse data detecting apparatus 100 measures a blood flow rate from an absorption amount of light with a certain wavelength that changes with the blood flow rate of a capillary vessel 201 inside the body, and detects pulses from that change.

Meanwhile, the pulse data detecting apparatus 100 disclosed in the above-described patent documents, etc., is influenced by the condition of the body surface to be measured, for example, uncertainties such as unevenness in distribution of lentigines (moles), body hair, body color, capillary vessels on the skin surface and in changes of blood pressure. As a result, extremely large unevenness may occur in the measurement result. In particular, in an environment with adverse conditions, ratios of disturbance noises such as ambient light, device vibrations, and a shift of a measurement region and disturbance noises such as changes of blood flows due to body movement originally included in blood flow components are increased, and thereby pulses cannot be accurately detected.

SUMMARY OF THE INVENTION

In light of the above-described problems, an object of the present invention is to provide a pulse data detecting apparatus, pulse data detecting method, and pulse data detection program capable of suppressing an influence of the condition of the body surface to be measured and obtaining an appropriate measurement result under a wide range of conditions.

A pulse data detecting apparatus according to the present invention comprising: a pulse data detecting section which detects pulse data as being in contact with a body surface; a blood-flow suppressing section which suppresses a blood flow in a blood vessel to increase a blood pressure of a measurement region; and a pulse data output section which outputs the pulse data detected by the pulse data detecting section in a state where the blood-flow suppressing section suppresses the blood flow in the blood vessel.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 2A and FIG. 2B are perspective views of external appearance of the pulse data detecting apparatus 1 according to the first embodiment;

FIG. 3 is a flowchart of a pulse data detecting method performed by the pulse data detecting apparatus 1 according to the first embodiment;

FIG. 4A and FIG. 4B are cross-sectional views for describing a pulse data detecting method performed by a pulse data detecting apparatus 1 according to the first embodiment;

FIG. 6A, FIG. 6B and FIG. 6C are schematic diagrams of examples of mounting the pulse data detecting apparatus 1 according to the first and second embodiments of the present invention;

FIG. 10 is a flowchart of a specific example when a specific scheme of a method of judging an appropriate set value of a protrusion amount of the blood-flow-suppressing projection 21 is applied to the pulse data detecting method according to the present invention;

FIG. 14A and FIG. 14B are diagrams each depicting a third example of measurement data obtained by the pulse data detecting method according to the present specific example and analysis data obtained by frequency analysis; and FIG. 15 is a flowchart of another example of the method of judging an appropriate set value of a protrusion amount of the blood-flow-suppressing projection 21 applied to the present specific example;

DETAILED DESCRIPTION OF THE PREFERRED EMBODIMENTS

Figure 1:
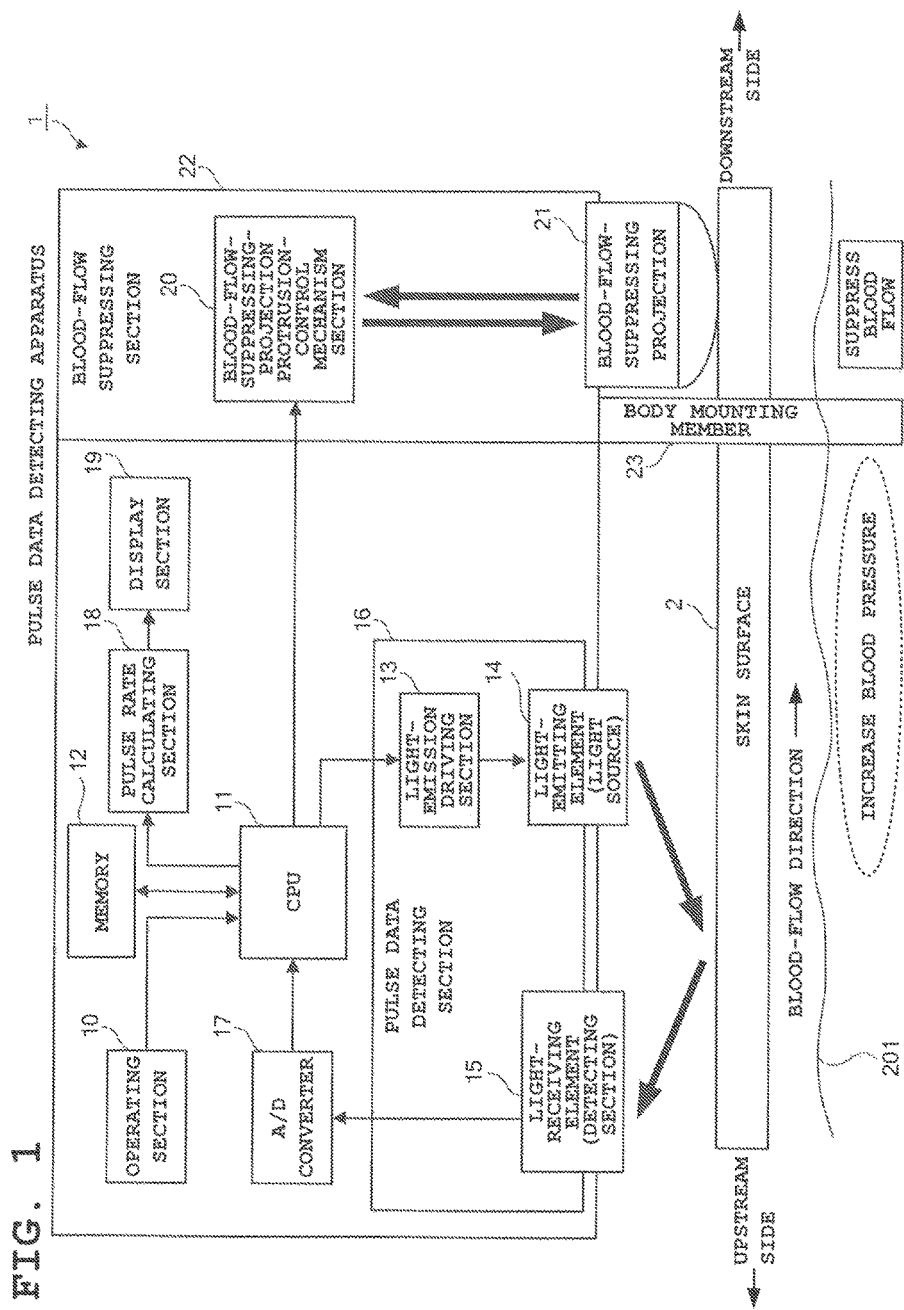
FIG. 1 is a block diagram of one example of a structure of a pulse data detecting apparatus 1 according to a first embodiment of the present invention.

The pulse data detecting apparatus, pulse data detecting method, and pulse data detection program according to the present invention are described in detail below with embodiments. The following description is made in the case where a reflective-type optical pulse data detecting apparatus is applied. Basically, in the case where a transmission-type one is applied, similar structure and operation have as well A. First Embodiment FIG. 1 is a block diagram of one example of a structure of a pulse data detecting apparatus 1 according to a first embodiment of the present invention. In FIG. 1, the pulse data detecting apparatus 1 includes an operating section 10, a CPU 11, a memory 12, a light-emission driving section 13, light-emitting element (light source) 14, light-receiving element (detecting section) 15, a pulse data detecting section 16, an A/D converter 17, a pulse rate calculating section 18, a display section 19, a blood-flow-suppressing-projection protrusion-control mechanism section 20, blood-flow-suppressing projection 21, and a body mounting member 23.

The operating section 10 has, for example, a power supply switch operated by a user as a test subject and an operation control switch for controlling the start and stop of a sensing operation. The CPU 11 performs processing by following a control program stored in the memory 12, and thereby controls pulse measurement, calculation of a pulse rate, and a display operation of the pulse rate. More specifically, the CPU 11 feeds back to the light-emission driving section 13 to cause the light-emitting element 14 to emit light, controls the blood-flow-suppressing-projection protrusion-control mechanism section 20 to control a protrusion amount of the blood-flow-suppressing projection 21 in a stepwise manner, and determines a protrusion amount of the blood-flow-suppressing projection 21 satisfying a predetermined condition based on an electrical signal (output signal) outputted according to the light amount detected by the light-receiving element 15 at each step.

The memory 12 stores measurement data, a control program, data generated at the time of executing the control program, and the like. The light-emission driving section 13 causes the light-emitting element 14 with a predetermined light emission amount, by following the control from the CPU 11. The light-emitting element (light source) 14 is made of an LED or the like, and at least one of light-emitting elements is arranged on a bottom of a housing (a surface which abuts on a skin surface 2). By following the driving control of the light-emission driving section 13, the light-emitting element (light source) 14 irradiates the skin surface 2 with a predetermined light emission amount of visible light (for example, green visible light of a wavelength of approximately 525 nm). The reflective-type detecting method using visible light is advantageously less prone to be influenced by reflected light from blood flows in veins and arteries that are present deeply inside the body because of low transmittance of visible light inside the body and also is less prone to be influenced by a propagation time lag in heartbeats occurring in each blood vessel due to blood flow path length.

The light-receiving element (detecting section) 15 is made of an illuminance sensor, a photodiode, or the like, and at least one of light-receiving elements are arranged on the bottom of the housing (the surface which abuts on the skin surface 2). The light-receiving element (detecting section) 15 receives reflected light emitted from the light-emitting element (light source) 14 and reflected on the skin surface 2, and outputs an output signal according to the light reception amount or light reception intensity. The light-emission driving section 13, the light-emitting element 14, and the light-receiving element 15 form a pulse data detecting section 16.

The A/D converter 17 converts the output signal from the light-receiving element 15 to digital data (sensor data), and supplies the digital data to the CPU 11. The pulse rate calculating section 18 performs processing by following a predetermined algorithm program, and thereby processes the sensor data obtained by the light-receiving element 15 with the protrusion amount of the blood-flow-suppressing projection 21 satisfying the predetermined condition and determined by the CPU 11 to calculate a pulse rate. The pulse rate calculating section 18 may be a computation function incorporated in the CPU 11. Also, the present invention is not limited to a pulse rate and, as will be described further below, various information regarding blood flows included in pulse waveform data (pulse wave data) may be calculated for output.

The display section 19 has, for example, a display device such as a liquid-crystal display panel or an organic EL display panel capable of color or monochrome display, displaying the pulse rate calculated by the pulse rate calculating section 18. The display section 19 is not limited thereto. As described above, as pulse data, pulse waves (specifically, pulse waveform data), pitch, and the like may be displayed. For example, pulse waveform data (pulse wave data) includes various information regarding blood flows. That is, the pulse data can be applied as an important parameter for fudging health and exercise condition (such as clogging of blood vessels, blood vessel age, and judgment of a tension state), a workout state, and the like. The display section 19 may display the judgment results by using specific character information, light emission pattern, or the like.

The blood-flow-suppressing-projection protrusion-control mechanism section 20 controls driving of the blood-flow-suppressing projection 21 under the control of the CPU 11, and thereby controls the protrusion amount of the blood-flow-suppressing projection 21 in a stepwise manner. The blood-flow-suppressing projection 21 is driving-controlled by the blood-flow-suppressing-projection protrusion-control mechanism section 20, and is structured to press or compress the skin surface 2 of a user as a test subject with a tip formed of an elastic member. The body mounting member 23 is formed of a flexible belt-shaped member for fixing (a skin contact surface of) the pulse data detecting apparatus 1 onto the body of the user.

FIG. 2A and FIG. 2B are perspective views of external appearance of the pulse data detecting apparatus 1 according to the present first embodiment. FIG. 2A depicts the external appearance of the pulse data detecting apparatus 1 having the blood-flow-suppressing projection 21 retracted therein. FIG. 2B depicts the external appearance of the pulse data detecting apparatus 1 with the blood-flow-suppressing projection 21 protruding therefrom. In FIG. 2A and FIG. 2B, the light-emitting element 14, the light-receiving element 15, and the blood-flow-suppressing projection 21 are arranged with a predetermined space apart from one another on a circuit board 24 having various circuits mounted thereon. Around the light-emitting element 14, the light-receiving element 15, and the blood-flow-suppressing projection 21, a light-shielding block 25 is arranged.

Here, originally, the pulse data detecting apparatus 1 can measure pulses even with the structure where the light-shielding block 25 is not arranged. In the present embodiment, in addition to reflection from the body surface, direct light due to wrapping from an element side surface may have extremely large influence. For the purpose of eliminating direct light, the light-shielding block 25 is arranged around the light-emitting element 14 and the light-receiving element 15. As the light-shielding block 25, a component formed of black resin or the like can be applied. Also, FIG. 2A and FIG. 2B depict the case where the height of the light-shielding block 25 from the upper surface of the circuit board 24 are formed to be higher than those of the light-emitting element 14 and light-receiving element 15. In this structure, the upper surface of the light-shielding block 25 serves as a skin contact surface in contact with the skin surface when the pulse data detecting apparatus 1 is mounted on the user. The light-shielding block may not be formed such that the height of light-shielding block is contact with the skin surface, and may not be formed of a single black resin component.

By following driving control of the blood-flow-suppressing-projection protrusion-control mechanism section 20, the blood-flow-suppressing projection 21 purposely presses or compresses a region on a side corresponding to a downstream of a blood flow by protruding at the time of pulse measurement. As a result, a downstream portion of the blood vessel is pressed or compressed, whereby the blood pressure of the measurement region is temporarily increased and an output of the blood flow is increased. Accordingly, an output signal at a sufficient output level can be obtained from the light-receiving element 15. In the present embodiment, as depicted in FIG. 2A and FIG. 2B, the blood-flow-suppressing projection 21 is retracted in the light-shielding block 25 arranged, around the light-emitting element 14 and the light-receiving element 15, and protrudes over the height of the light-shielding block 25 (that is, the height of the skin contact surface) at the time of pulse measurement. The present invention is not limited to the structure where the blood-flow-suppressing projection 21 is caused to protrude with reference to the height of the light-shielding block, and the blood-flow-suppressing projection 21 may have any structure as long as the blood-flow-suppressing projection 21 is caused to protrude so as to press or compress a region on the downstream side of the blood flow for the purpose of increasing the blood pressure of the measurement region as described above.

Next, a pulse data detecting method by the pulse data detecting apparatus 1 according to the first embodiment is described.

FIG. 3 is a flowchart of the pulse data detecting method performed by the pulse data detecting apparatus 1 according to the present first embodiment. The user first wears the above-described pulse data detecting apparatus 1 on a measurement region (for example, the wrist or earlobe), and performs a predetermined operation (starts measurement) from the operating section 10. When an instruction for starting measurement is provided from the user, the CPU 11 performs various processing by following the flowchart depicted in FIG. 3.

First at Step S10, the CPU 11 performs preparation of starting measurement. Next, the CPU 11 sets a set value A (a predetermined protrusion amount) of the blood-flow-suppressing projection 21 at Step S12, and controls the light-emission driving section 13 to cause the light-emitting element 14 to light up at Step S14. The set value A (predetermined protrusion amount) may be set by measuring an average protrusion amount in advance, or may be automatically set according to the hardness (repulsion, force) of the skin surface 2 to be pressed by the blood-flow-suppressing projection 21. Next at Step S16, the CPU 11 controls the blood-flow-suppressing-projection protrusion-control mechanism section 20 to set the protrusion amount of the blood-flow-suppressing projection 21 at the set value A. Next at Step S18, the blood-flow-suppressing-projection protrusion-control mechanism section 20 confirms completion of setting (protrusion) of the blood-flow-suppressing projection 21. Next at Step S20, the CPU 11 causes measurement of an output from the light-receiving element 15 receiving reflected light emitted from the light-emitting element 14 and reflected from the skin surface 2. Next at Step S22, the CPU 11 causes an output signal from the light-receiving element 15 to be outputted to the A/D converter 17. As a result the CPU 11 captures an output value (sensor data) from the light-receiving element 15 when the skin surface 2 is pressed or compressed by the blood-flow-suppressing projection 21 protruding with the protrusion amount represented by the set value A. The CPU 11 then associates the set value A (protrusion amount) of the blood-flow-suppressing projection 21 and the captured output value (sensor data) from the light-receiving element 15 with each other, and temporarily stores the resultant data as measurement data in a predetermined storage area of the memory 12.

Next at Step S24, the CPU 11 performs computation processing on the output value (sensor data waveform signal) from the light-receiving element 15 with respect to the set value A of the blood-flow-suppressing projection 21. The pulse rate calculating section 18 calculates a pulse rate (in general, the number of peaks in a waveform for one minute) at Step S26, and outputs the calculated pulse rate to the display section 19 at Step S28. Next, at Step S30, the display section 19 displays the calculated pulse rate (numerical value data) as pulse data. The pulse data is not limited to the pulse rate, and measurement of pulse waveform data (pulse wave data) or the like can also be directly applied. Also, the pulse rate calculated at the pulse rate calculating section 18 is associated with, for example, time data at the time of measurement, and is stored in a predetermined storage area of the memory 12.

Next at Step S32, the CPU 11 judges whether an end instruction is provided to the operating section 10 from the user. When an end instruction is not provided (NO at Step S32), the CPU 11 returns to Step S10, repeating the above-described processing. On the other hand, when an end instruction is provided from the user (YES at Step S32), the CPU 11 performs predetermined end processing (such as storing the pulse rate and discarding measurement data) at Step S34, and then ends the processing.

FIG. 4A and FIG. 45 are cross-sectional views for describing the pulse data detecting method performed by the pulse data detecting apparatus 1 according to the present first embodiment. By following driving control by the blood-flow-suppressing-projection protrusion-control mechanism section 20, the blood-flow-suppressing projection 21 is retracted inside the light-shielding block 25 except at the time of measurement as depicted in FIG. 4A, and protrudes over the height of the light-shielding block 25 at the time of measurement as depicted in FIG. 4B. The pulse data detecting apparatus 1 is mounted on the body such that the blood-flow-suppressing projection 21 is arranged on the downstream side (in the depicted example, on a heart side) of the blood flow with respect to the pulse data detecting section including the light-emitting element 14 and the light-receiving element 15, etc.

As depicted in FIG. 4B, the blood-flow-suppressing projection 21 protrudes with the predetermined protrusion amount at the time of pulse measurement, and thereby purposely presses or compresses a region on the downstream side of the blood flow. As a result, a downstream portion of a capillary vessel 201 is pressed or compressed (i.e. by being pressed or compressed, the blood flow amount is decreased). Thus, the blood pressure of the measurement region (a region where the light-emitting element 14 and the light-receiving element 15 face the skin surface 2) temporarily increases, whereby the output of the blood flow increases.

In pulse measurement with the capillary vessel 201, it has been revealed that the blood flow amount is basically proportional to the blood pressure. The increase of blood pressure causes the increase of the blood flow amount approximately proportional thereto, and thereby tends to be reflected onto a change in color of the body surface. Accordingly, even when a sufficient output level from the light-receiving element 15 cannot be obtained for a certain measurement region as depicted in FIG. 4A, an appropriate output satisfying a predetermined condition can be obtained by performing control such that the blood-flow-suppressing projection 21 placed downstream of that measurement region purposely press or compress the blood vessel as depicted in FIG. 4B. Note that the blood-flow-suppressing projection 21 is not to completely stop the blood flow by pressing and compression, but to promote an increase in blood pressure. Accordingly, it is enough for the blood-flow-suppressing projection 21 to press or compress the measurement region by a force to the extent of lightly pressing the body surface with a finger.

As described above, according to the present first embodiment, the blood-flow-suppressing projection 21 placed downstream of the measurement region is caused to protrude, and thereby purposely presses or compresses the blood vessel to suppress the blood flow. Accordingly, an optimum output satisfying a predetermined condition (an adequate condition) from the light-receiving element 15 or an appropriate output in a specific range including the optimum output (hereinafter collectively referred to as an "appropriate output") can be obtained, and stable pulse measurement can be performed regardless of the state of placement of the pulse data detecting apparatus 1 on the human body, B. Second Embodiment Next, a second embodiment according to the present invention is described.

The structure and construction, etc., of a pulse data detecting apparatus 1 according to the present second embodiment are similar to those of the above-described first embodiment (refer to FIG. 1, FIG. 2A and FIG. 2B), and therefore are not described herein. In the present second embodiment, the protrusion amount of the blood-flow-suppressing projection 21 placed downstream of the measurement region is controlled in a stepwise manner. As a result, while the force for purposely pressing or compressing the blood vessel is being changed in a stepwise manner, the output value (sensor data) from the light-receiving element 15 is sequentially captured, output values with all protrusion amounts are compared with each other, and an appropriate output satisfying a predetermined condition is obtained.

Next, a pulse data detecting method by the pulse data detecting apparatus 1 according to the second embodiment described above is described.

Figure 5:
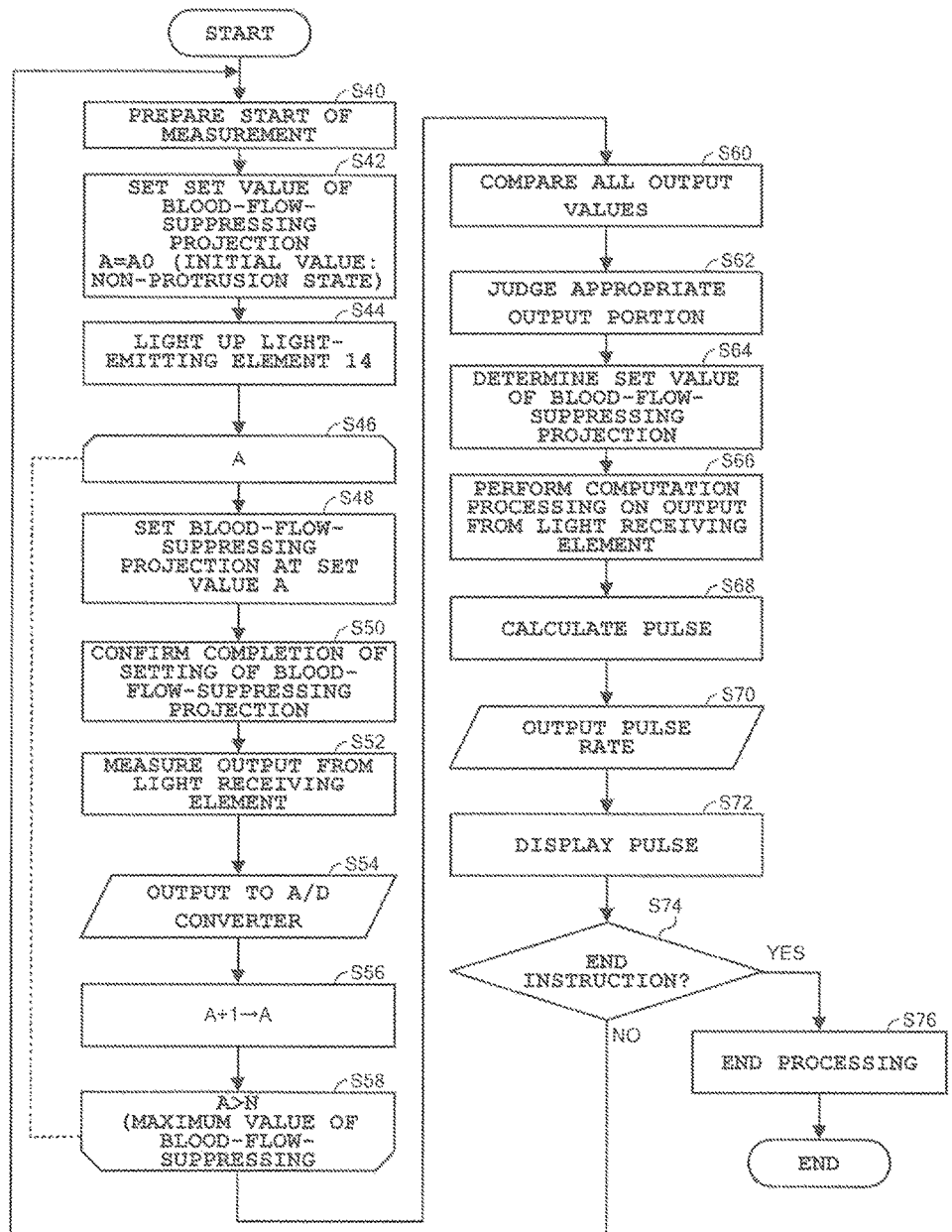
FIG. 5 is a flowchart of a pulse data detecting method performed by a pulse data detecting apparatus 1 according to a second embodiment.

FIG. 5 is a flowchart of the pulse data detecting method performed by the pulse data detecting apparatus 1 according to the present second embodiment. The user first wears the above-described pulse data detecting apparatus 1 on a measurement region (for example, the wrist or earlobe), and performs a predetermined operation (starts measurement) from the operating section 10. When an instruction for starting measurement is provided from the user, the CPU 11 performs various processing by following the flowchart depicted in FIG. 5.

First at Step S40, the CPU 11 performs preparation of starting measurement, Next, the CPU 11 sets the set value A of the blood-flow-suppressing projection 21 at an initial value A0 (A=A0) for a non-protrusion state at Step S42, and controls the light-emission driving section 13 to cause the light-emitting element 14 to light up at Step S44. The set value A indicates a protrusion amount of the blood-flow-suppressing projection 21 (may be a multiplication coefficient with respect to a unit length), and takes a value of A0 to N (a maximum value of the protrusion amount). Next, as incrementing the set value A by 1, the CPU 11 repeats processing at Step S46 to Step S58. Here, the initial value A0 or the set value A of the blood-flow-suppressing projection 21 set by increment by the CPU11 is temporarily stored in, for example, the memory 12. The series of processing at Step S46 to Step S58 is described in detail below.

First at Step S46, the CPU 11 reads out the set value A from the memory 12. At Step S48, the CPU 11 controls the blood-flow-suppressing-projection protrusion-control mechanism section 20 to set the protrusion amount of the blood-flow-suppressing projection 21 at the set value A. Next at Step S50, the blood-flow-suppressing-projection protrusion-control mechanism section 20 confirms completion of setting (protrusion) of the blood-flow-suppressing projection 21. Next at Step S52, the CPU 11 causes measurement of an output from the light-emitting element 15. Here, in the state where the set value A is set at the initial value A0, the blood-flow-suppressing-projection protrusion-control mechanism section 20 confirms a non-protrusion state of the blood-flow-suppressing projection 21, and the CPU 11 causes measurement of an output from the light-receiving element 15 in this state. Next at Step S54, an output signal from the light-receiving element 15 is outputted to the A/D converter 17. As a result, the CPU 11 first captures an output value (sensor data) from the light-receiving element 15 when the skin surface 2 is pressed or compressed by the blood-flow-suppressing projection 21 protruding with the protrusion amount represented by the set value A (=A0) (that is, when the blood-flow-suppressing projection 21 is set to be in a non-protrusion state and does not press or compress the skin surface 2). The CPU 11 associates the set value A (protrusion amount) of the blood-flow-suppressing projection 21 at this moment and the captured output value (sensor data) from the light-receiving element 15 with each other, and temporarily stores the resultant data as measurement data in a predetermined storage area of the memory 12.

Next at Step S56, the CPU 11 increments the set value A by 1 (A+1→A=1). The incremented set value A is temporarily stored in, for example, the memory 12. Then at Step S58, when the set value A is not larger than the maximum value N, the CPU 11 returns to Step S46, repeating measurement with the light-receiving element 15 when the protrusion amount of the blood-flow-suppressing projection 21 is set at the set value A (=1) That is, at Step S46 to Step S58, as changing the protrusion amount of the blood-flow-suppressing projection 21 in a stepwise manner according to the set value A (=A0, 1, 2, . . . , N) (that is, as changing a pressing force or compression force to the skin surface 2), the CPU 11 sequentially captures output values (sensor data) from the light-receiving element 15 and stores the captured values in a predetermined storage area of the memory 12.

Then at Step S58, when the set value A is larger than the maximum value N, the CPU 11 compares the output values with all set values A (protrusion amount) stored in the memory 12 with each other at Step S60, and judges an appropriate output portion at Step S62. In "judging an appropriate output portion", based on composite factors such as whether the magnitude of the output level is sufficient and whether the S/N ratio (signal-to-noise ratio) has a value capable of sufficiently extracting a signal, the CPU 11 judges an appropriate output. Here, the CPU 11 judges an appropriate output based on whether the output is at least within a specific range set in advance or whether the output satisfies a specific threshold or condition. A scheme of judging an appropriate output portion (a method of judging an appropriate set value) will be described in detail further below.

Then at Step S64, the CPU 11 determines the set value A of the blood-flow-suppressing projection 21 when the output is judged as appropriate. Next at Step S66, the CPU 11 performs computation processing on the output value (sensor data waveform signal) from the light-receiving element 15 with respect to the set value A of the blood-flow-suppressing projection 21 when the output is judged as appropriate. Furthermore, the pulse rate calculating section 18 calculates a pulse rate (in general, the number of peaks in a waveform for one minute) at Step S66, and outputs the calculated pulse rate to the display section 19 at Step S70. Next at Step S72, the display section 19 displays the calculated pulse rate (numerical value data) as pulse data. The pulse data is not limited to a pulse rate, and measurement of pulse waveform data (pulse wave data) or the like can also be directly applied. Also, the pulse rate calculated at the pulse rate calculating section 18 is associated with the set value A (protrusion amount) of the blood-flow-suppressing projection 21 when the output is judged as appropriate and time data at the time of measurement etc., and is stored in a predetermined storage area of the memory 12.

Next at Step S74, the CPU 11 judges whether an end instruction is provided to the operating section 10 from the user. When an end instruction is not provided (NO at Step S74), the CPU 11 returns to Step S40, repeating the above-described processing. On the other hand, when an end instruction is provided from the user (YES at Step S74), the CPU 11 performs predetermined end processing (such as storing the pulse rate and discarding measurement data) at Step S76, and then ends the processing.

As described above, according to the present second embodiment, as changing the force for purposely pressing or compressing the blood vessel in a stepwise manner by controlling the protrusion amount of the blood-flow-suppressing projection 21 placed downstream of the measurement region in a stepwise manner, an appropriate output satisfying a predetermined condition is obtained from the light-receiving element 15. Accordingly, an appropriate output level can be obtained regardless of the state of placement of the pulse data detecting apparatus 1 on the human body, and thereby stable pulse measurement can be performed.

C. Examples of Mounting Pulse Data Detecting Apparatus

Next, examples of mounting the pulse data detecting apparatus 1 according to the above-described first and second embodiments on the human body are described.

FIG. 6A, FIG. 6B, and FIG. 6C are schematic diagrams of examples of mounting the pulse data detecting apparatus 1 according to the first and second embodiments described above. FIG. 6A depicts a state where the pulse data detecting apparatus 1 is mounted on the wrist with the body mounting member 23 formed in a belt shape. FIG. 6E depicts a state where the pulse data detecting apparatus 1 is mounted on the index finger with the body mounting member 23 formed in a belt shape. FIG. 6C depicts a state where the pulse data detecting apparatus 1 is mounted on the index finger with the body mounting member 23 formed in a bag shape (a finger sack). In any of these mounting examples, it is important to mount the pulse data detecting apparatus 1 so that the blood-flow-suppressing projection 21 is arranged on the downstream side of the blood flow at the measurement region. These mounting examples are merely examples, and the present invention is not limited thereto. Basically, any mode can be taken as long as the pulse data detecting apparatus 1 is mounted on a region corresponding to an end of the human body.

D. Specific Examples of Blood-Flow-Suppressing Projection

Next, specific examples of structure of the blood-flow-suppressing projection of the pulse data detecting apparatus according to the above-described first and second embodiments are described.

Figure 7A:
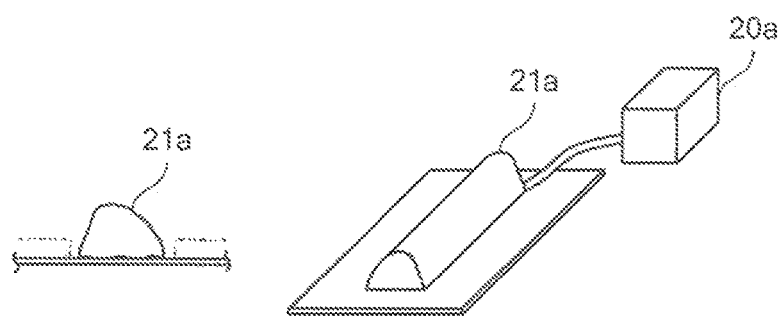
FIG. 7A and FIG. 7B are schematic views of a first specific example of a blood-flow-suppressing projection 21 of the pulse data detecting apparatus 1 according to the first and second embodiment of the present invention.
Figure 7B:
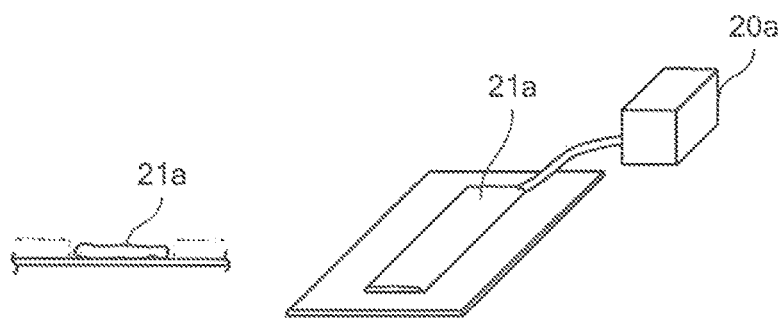

FIG. 7A and FIG. 7B are schematic view of a first specific example of a blood-flow-suppressing projection 21a of the pulse data detecting apparatus 1 according to the first and second embodiment described above. In the examples depicted in FIG. 7A and FIG. 7B, a blood-flow-suppressing projection 21a is assumed to be a hermetic bag in a balloon shape (or a bag shape), and is fed with air (fluid including gas, liquid, and powder) from the blood-flow-suppressing-projection protrusion-control mechanism section (small-sized compressor) 20a to be swelled or is suctioned to be deflated, whereby the protrusion amount of the blood-flow-suppressing projection 21a is controlled. FIG. 7A depicts a state where air is fed from a blood-flow-suppressing-projection protrusion-control mechanism section 20a to the blood-flow-suppressing projection 21a to swell the blood-flow-suppressing projection 21a. FIG. 7B depicts a state where air is suctioned to deflate the blood-flow-suppressing projection 21a.

Figure 8A:
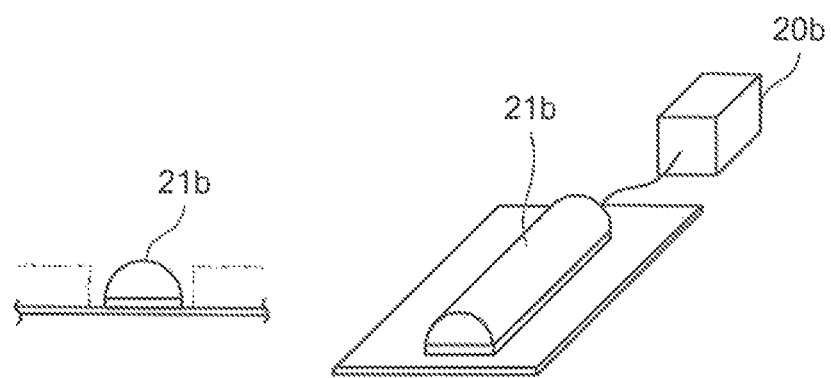
FIG. 8A and FIG. 8B are schematic view of a second specific example of the blood-flow-suppressing projection 21 of the pulse data detecting apparatus 1 according to the first and second embodiment of the present invention.
Figure 8B:
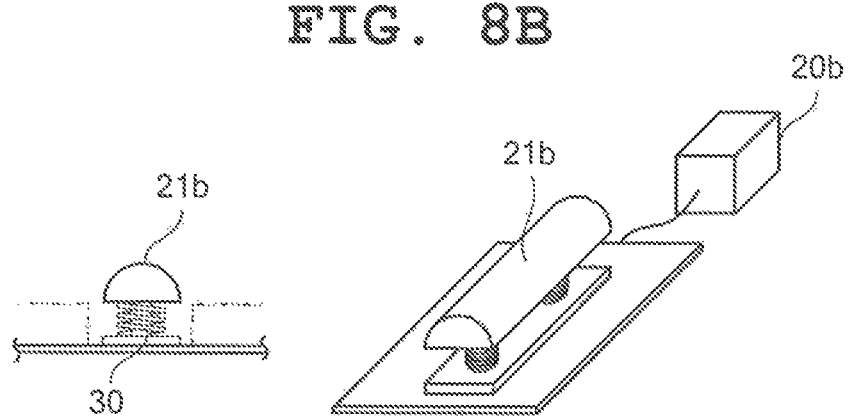

FIG. 8A and FIG. 8B are schematic view of a second specific example of a blood-flow-suppressing projection 21b of the pulse data detecting apparatus 1 according to the first and second embodiment described above. In the examples depicted in FIG. 8A and FIG. 8B, the blood-flow-suppressing projection 21b is a solid projection in a barrel shape (a columnar member having a semi-circular cross section). By driving a solenoid or mechanical mechanism by a blood-flow-suppressing-projection protrusion-control mechanism section 20b, the protrusion amount of the blood-flow-suppressing projection 21b is controlled. On a lower part of the blood-flow-suppressing projection 21b, a coil spring 30 is provided for the purpose of automatic retracting at the time of non-operation. FIG. 8A depicts a state where the blood-flow-suppressing projection 21b is retracted. FIG. 8B depicts a state where the solenoid or mechanical mechanism is driven by the blood-flow-suppressing-projection protrusion-control mechanism section 20b to protrude the blood-flow-suppressing projection 21b.

Figure 9A:
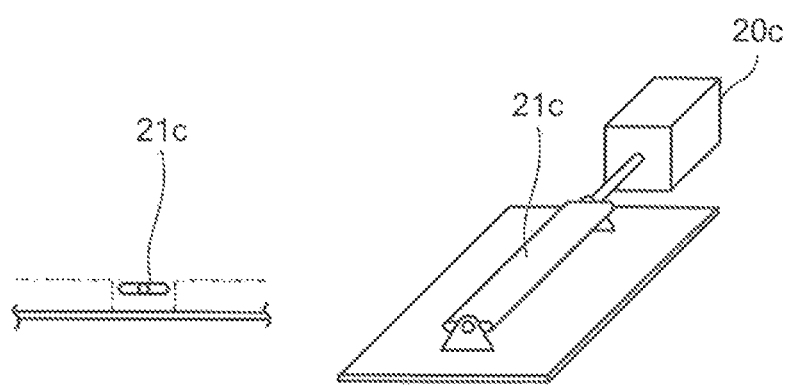
FIG. 9A and FIG. 9B are schematic view of a third specific example of the blood-flow-suppressing projection 21 of the pulse data detecting apparatus 1 according to the first and second embodiment of the present invention.
Figure 9B:
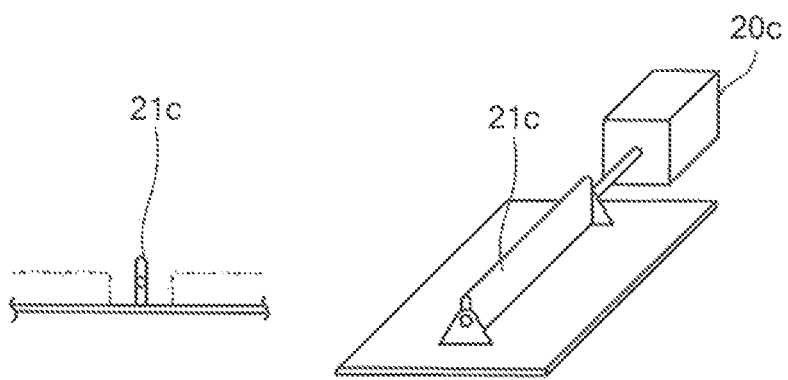

FIG. 9A and FIG. 9B are schematic view of a third specific example of the blood-flow-suppressing projection 21 of the pulse data detecting apparatus 1 according to the first and second embodiment described above. In the examples depicted in FIG. 9A and FIG. 9B, a blood-flow-suppressing projection 21c is a flat-shaped solid member. By rotating the blood-flow-suppressing projection 21c by a blood-flow-suppressing-projection protrusion-control mechanism section 20c, the protrusion amount (protrusion height) of the blood-flow-suppressing projection 21c is controlled. FIG. 9A depicts a state where the blood-flow-suppressing projection 21c is retracted by being made parallel to the skin surface 2 (or the upper surface of the light-shielding block 25). FIG. 9B depicts a state where the blood-flow-suppressing projection 21c is rotated by the blood-flow-suppressing-projection protrusion-control mechanism section 20c by 90 degrees to protrude.

In the above-described first and second embodiments, the pulse measurement period and measurement time are arbitrarily set according to the use purpose of the pulse data, measurement accuracy, and the like. In general, the measurement time requires, on the order of ten to fifteen seconds, or several seconds to one minute depending on the measurement state. The time from when pressing or compression is performed to when the pressing or compression is reflected onto the blood flow and blood pressure is approximately within one second. Accordingly, there is little limitation in the relation between the scheme for compression and a temporal factor regarding measurement.

Also, in the above-described first and second embodiments the blood flow can be suppressed by the blood-flow-suppressing projection 21 even without the body mounting member 23. For example, the blood-flow-suppressing projection 21 may be protruded from a table-like flat surface having the pulse data detecting section 16 and a blood-flow suppressing section 22 incorporated therein, with a human body being placed on the flat surface.

Additionally, in the above-described first and second embodiments, the pulse rate (in general, the number of peaks in a waveform for one minute) calculated by the pulse rate calculating section 18 may be outputted to an external display device and an analysis device, etc. Also in this case, the pulse data is not limited to a pulse rate, and measurement of pulse waveform data (pulse wave data) or the like can also be directly applied.

In the above-described second embodiment, in order to prevent a compressed state from continuing a long time, the protrusion amount of the blood-flow-suppressing projection 21 is set for pressing or compression at every detection with the light-receiving element 15. In other words, the blood-flow-suppressing projection 21 is retracted every time detection with the light-receiving element 15 ends. As a result, uncomfortable feeling of the user as a test subject caused by always pressing or compressing the skin surface can be reduced. Also, in order that pulse measurement continues for a long time in the case of pulse measurement during exercise or the like, when it is detected that the compression time has continued for a predetermined time (for example, five minutes) compression may be once released (the blood-flow-suppressing projection 21 may be retracted) to reduce the load on the user, and then a compressing operation may be performed again. In this case, while compression is being released, detection of pulse data may not be performed, and data complementation may be performed by assuming that similar pulse data is detected by using most recent data detected. This function is achieved by that the CPU 11 performs processing of controlling the blood-flow suppressing section 22 by counting time (for example, a reference clock) and thereby detecting the lapse of a predetermined time, or processing of complementing data by always holding latest pulse data which is most recently obtained during pulse measurement and using that the pulse data during compression release (measurement suspension).

Still further, in the present first and second embodiments, the blood flow in the blood vessel is suppressed by that the blood-flow-suppressing projection 21 presses or compresses the body surface. Accordingly, the output level of the light-receiving element 15 can be increased in a relatively simple structure.

Yet still further, in the present first and second embodiments, the blood-flow-suppressing projection 21 is arranged on the downstream side of the blood flow with respect to the position of placement of the pulse data detecting section 16, and the body surface is pressed or compressed on the downstream side of the blood flow. Accordingly, the blood pressure in the measurement region is effectively increased, and thereby the output level of the light-receiving element 15 can be increased.

Yet still further, in the present first and second embodiments, the blood-flow-suppressing projection 21 is structured to protrude in a skin direction by filling a bag-shaped member with a fluid including gas liquid, and powder to increase a volume thereof. Accordingly, the blood flow the blood vessel can be suppressed in a relatively simple structure, and the output level of the light-receiving element 15 can be increased.

Yet still further, in the present first and second embodiments, the blood-flow-suppressing projection 21 is structured to protrude by moving a stick-shaped member in the skin direction. Accordingly, the blood flow in the blood vessel can be suppressed in a relatively simple structure, and the output level of the light-receiving element 15 can be increased.

Yet still further, in the present first and second embodiments, the blood-flow-suppressing projection 21 is structured to protrude in the skin direction by rotating a flat member. Accordingly, the blood flow in the blood vessel can be suppressed in a relatively simple structure, and the output level of the light-receiving element 15 can be increased.

E. Specific Example of Pulse Data Detecting Method

Next, a method of judging an appropriate value of a set value defining the protrusion amount of the blood-flow-suppressing projection applied to the pulse data detecting method according to the above-described first and second embodiments (an appropriate set value) is described.

In the above-described first and second embodiments, it has been described that an appropriate output satisfying a predetermined condition can be obtained by the series of processing according to the pulse data detecting method (refer to the flowcharts depicted in FIG. 3 and FIG. 5). Here a method for judging "an appropriate output satisfying a predetermined condition" and a method for determining a set value (protrusion amount of the blood-flow-suppressing projection 21) from which the appropriate output can be obtained, are described, which are both applied to the above-described pulse data detecting method, in detail by specific schemes. In the following description, the appropriate output judging method and the appropriate set value determining method are collectively referred to as an "appropriate set value judging method" for convenience.

FIG. 10 is a flowchart of a specific example when a specific scheme of the method of judging an appropriate set value of a protrusion amount of the blood-flow-suppressing projection 21 is applied to the pulse data detecting method according to the present invention. Here, the case is described where a specific scheme of the appropriate set value judging method is applied to the pulse data detecting method in the above-described second embodiment. Note that processing procedures identical to those of the flowchart in the above-described second embodiment are provided with the same reference numeral.

In the pulse data detecting method according to the present specific example, the user first wears the pulse data detecting apparatus 1 on a measurement region (for example, the wrist or earlobe), and performs a predetermined operation (starts measurement) from the operating section 10. When instructed to start measurement from the user, the CPU 11 performs various processing by following the flowchart depicted in FIG. 10.

First at Step S110, the CPU 11 judges whether the set value A defining the protrusion amount of the blood-flow-suppressing projection 21 has been registered in advance in the memory 12. Here, a latest value judged as the most appropriate set value by a series of processing, which will be described further below, can be applied as a set value A registered in the memory 12. Then at Step S110, when a set value A has been registered in the memory 12 (YES at Step S110) the CPU 11 reads out the set value A from the memory 12, sets the read out value as a set value A for the blood-flow-suppressing projection 21 at Step S120, and performs processing at Step S166 onward, which will be described further below.

On the other hand, at Step S110, when a set value A has not been registered in the memory 12 (or when the set value A has been registered but is not the most appropriate value; NO at Step S110), as with the case in the above-described second embodiment, the CPU 11 performs a series of processing at Step S140 to S158 described below (corresponding to Step S40 to Step S58 of the second embodiment). That is, at Step S140, the CPU 11 performs preparation of starting measurement. The CPU 11 sets the set value A of the blood-flow-suppressing projection 21 at the initial value A0 (A=A0) for a non-protrusion state (protrusion amount=0) at Step S142, and controls the light-emissions driving section 13 to cause the light-emitting element 14 to light up at Step S144. Next, as incrementing the set value A by 1, the CPU 11 repeats processing at Step S146 to Step S158. Here, the initial value A0 or the set value A (=1 to N) of the blood-flow-suppressing projection 21 set by increment is temporarily stored in, for example, the memory 12.

First at Step S146, the CPU 11 reads out the set value A from the memory 12. At Step S148, the CPU 11 controls the blood-flow-suppressing-projection protrusion-control mechanism section 20 to set the protrusion amount of the blood-flow-suppressing projection 21 at the set value A. Next at Step S150, the blood-flow-suppressing-projection protrusion-control mechanism section 20 confirms completion of setting (protrusion) of the blood-flow-suppressing projection 21. Next, at Step S152, the CPU 11 causes measurement of an output from the light-emitting element 15. Here, in the present specific example, when reflected light emitted from the light-emitting element 14 and reflected on the skin surface 2 is received by the light-receiving element 15, the output according to light reception intensity is measured. Next at Step S154, an output signal from the light-receiving element 15 is outputted to the A/D converter 17. As a result, the CPU 11 captures an output value (sensor data) from the light-receiving element 15 when the skin surface 2 is pressed or compressed by the blood-flow-suppressing projection 21 protruding with the protrusion amount represented by the set value A. Here, when the set value A=A0, the blood-flow-suppressing projection 21 is set to be in a non-protrusion state. As a result, an output data (sensor data) from the light-receiving element 15 when the skin surface 2 is not pressed or compressed is captured. The CPU 11 associates the set value A (protrusion amount) of the blood-flow-suppressing projection 21 and the output value from the light-receiving element 15 at this moment with each other, and temporarily stores the resultant data as measurement data in a predetermined storage area of the memory 12. Here, the operation of measuring and capturing an output from the light-receiving element 15 at Step S152 and Step S154 continues for a predetermined time (for example, on the order of several seconds to one minute, preferably several tens of seconds or more), during which measurement data including a predetermined number of pulses (for example, five to forty-five pulses, preferably several tens of pulses or more) is obtained and is stored in the memory 12.

Next at Step S156, the CPU 11 increments the set value A by 1 (A+1→A=1). The incremented set value A is temporarily stored in, for example, the memory 12. Then at Step S158, when the set value A is not larger than the maximum value N, the CPU 11 returns to Step S146, repeating measurement with the light-receiving element 15 when the protrusion amount of the blood-flow-suppressing projection 21 is set at the set value A (=1) That is, at Step S146 to Step S158, as changing the protrusion amount of the blood-flow-suppressing projection 21 in a stepwise manner according to the set value A (=A0, 1, 2, . . . , N) (that is, as changing a pressing force or compression force to the skin surface 2), the CPU 11 sequentially captures output values (sensor data) from the light-receiving element 15 and stores the captured values in a predetermined storage area of the memory 12.

Then at Step S158, when the set value A is larger than the maximum value N, the CPU 11 judges an appropriate set value of the protrusion amount of the blood-flow-suppressing projection 21 at Step S200. Specifically, the CPU 11 applies a frequency analysis scheme by Fourier transform described below to perform processing of judging an appropriate set value of the blood-flow-suppressing projection (Step S210) and processing of registering the appropriate set value of the blood-flow-suppressing projection (Step S230).

(First Scheme)

Figure 11:
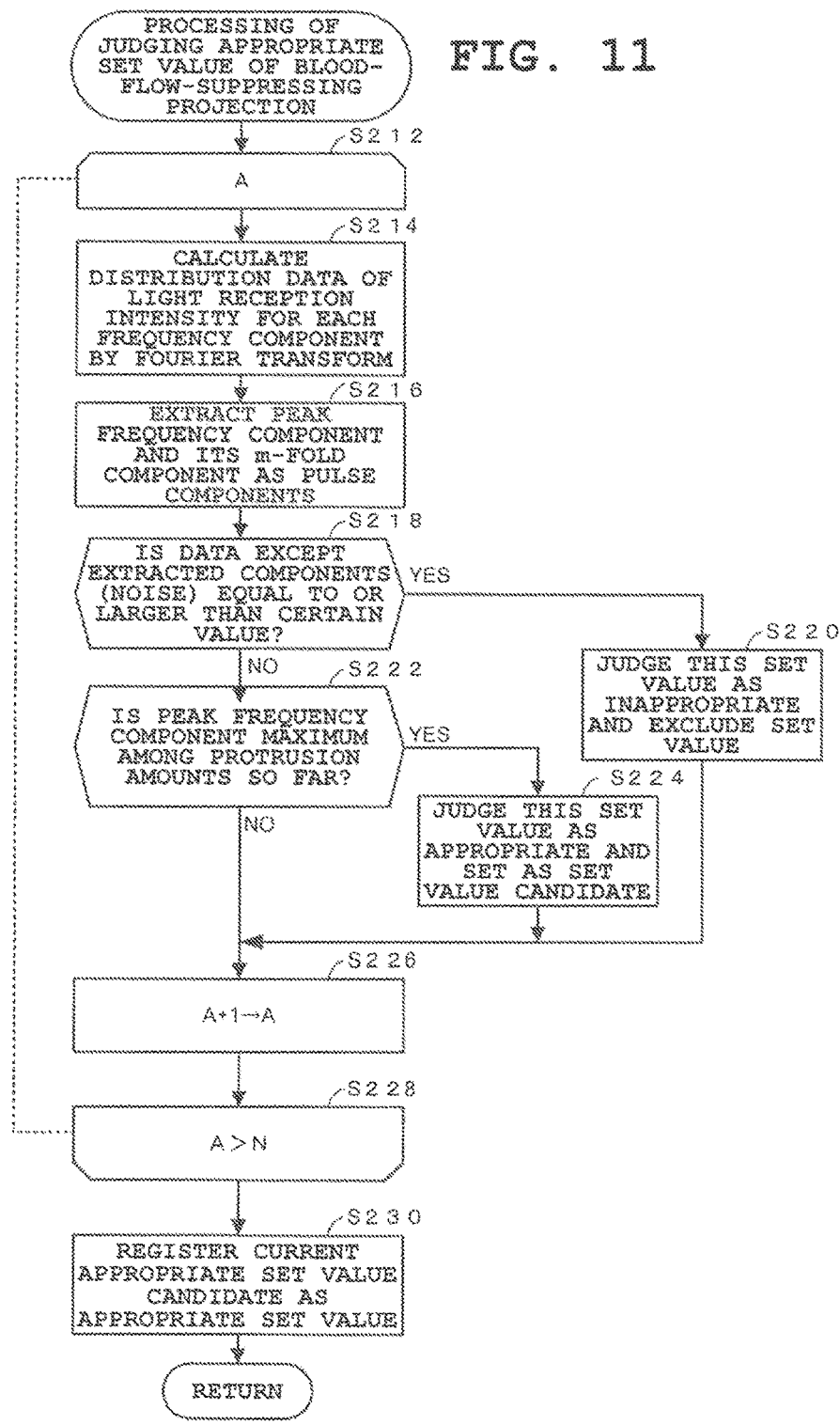
FIG. 11 is a flowchart of an example of the method of judging an appropriate set value of a protrusion amount of the blood-flow-suppressing projection 21 applied to the present specific example.
Figure 12A:
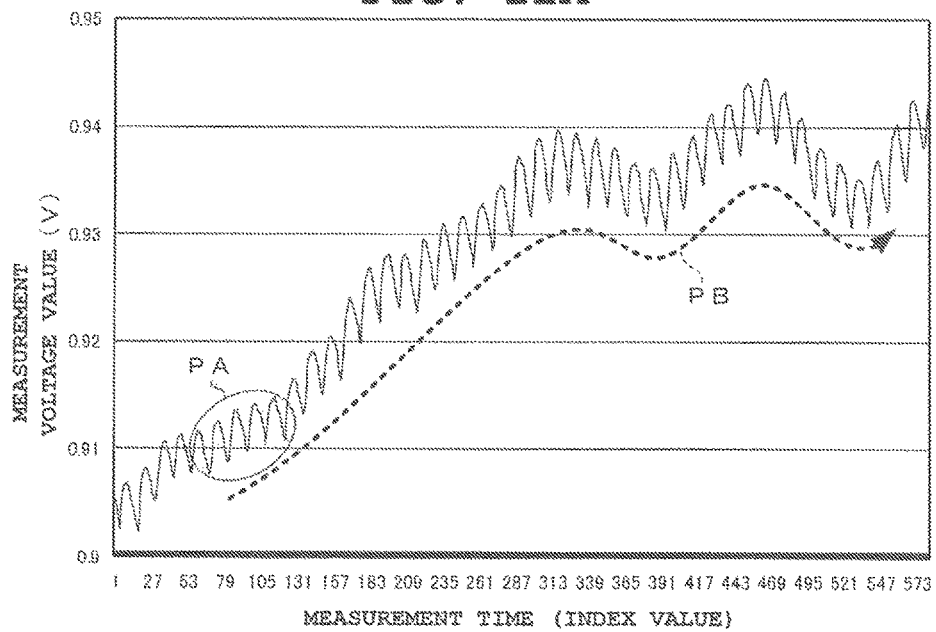
FIG. 12A and FIG. 12B are diagrams each depicting a first example of measurement data obtained by the pulse data detecting method according to the present specific example and analysis data obtained by frequency analysis.
Figure 12B:
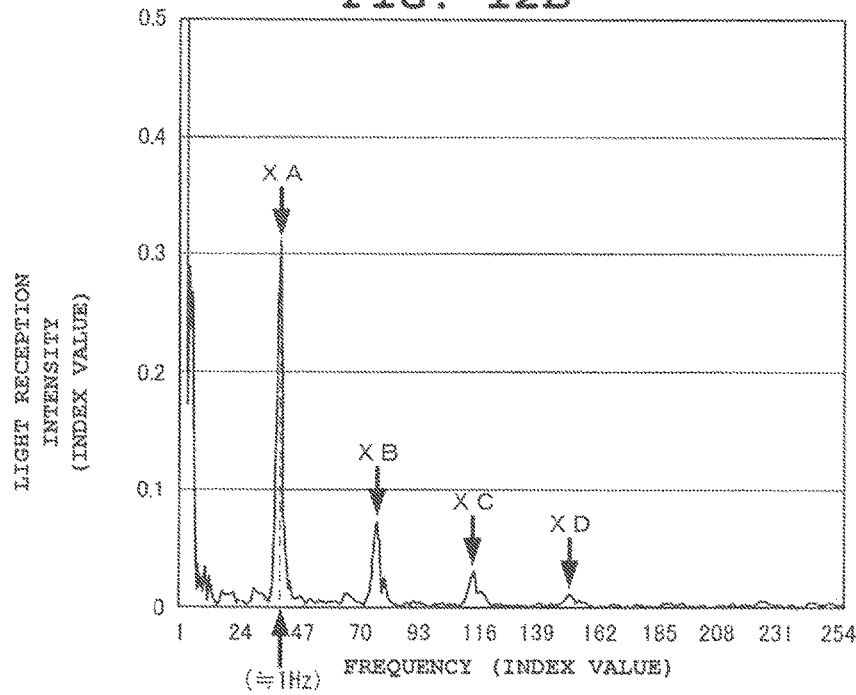
Figure 13A:
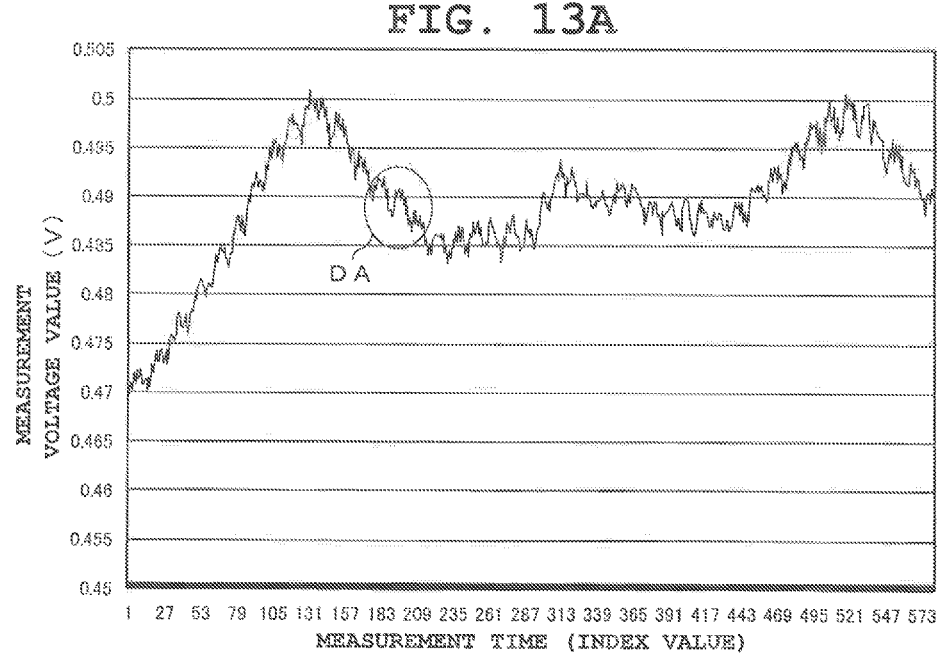
FIG. 13A and FIG. 13B are diagrams each depicting a second example of measurement data obtained by the pulse data detecting method according to the present specific example and analysis data obtained by frequency analysis.
Figure 13B:
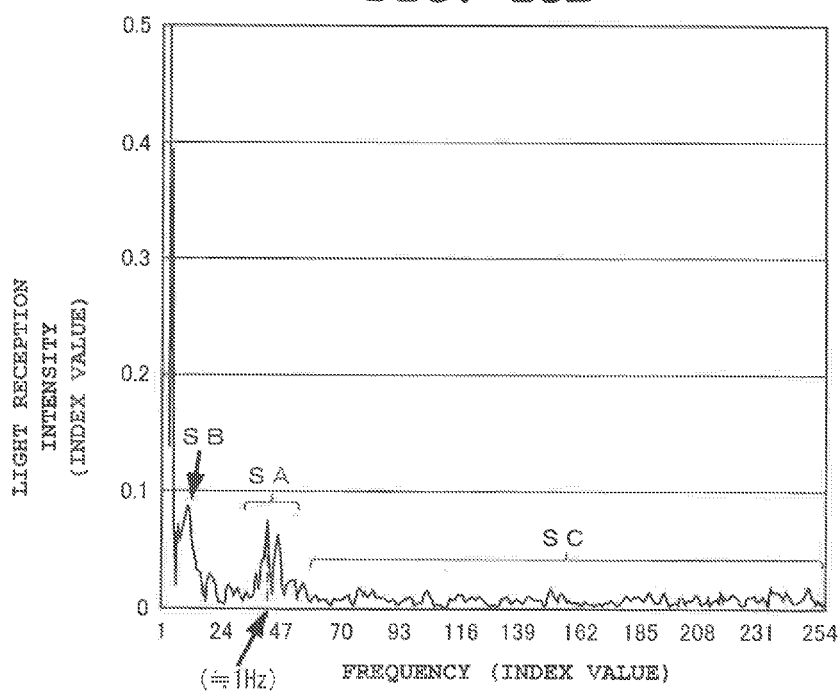
Figure 16:
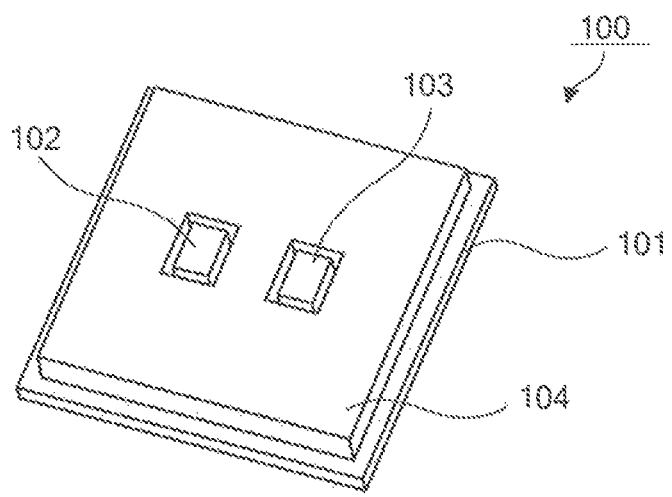
FIG. 16 is a perspective view of an example of external appearance, schematically depicting the structure of a pulse data detecting apparatus 100 as a comparison target of the present invention (conventional art)
Figure 17:
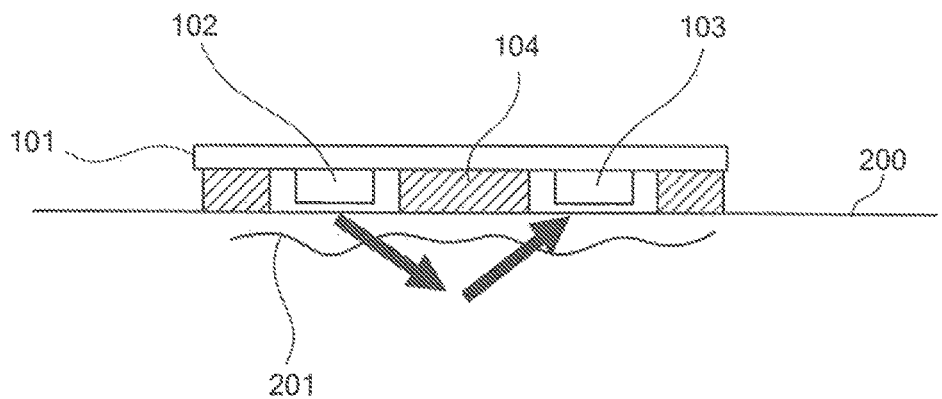
FIG. 17 is a cross-sectional view of the state of the pulse data detecting apparatus 100 as a comparison target of the present invention at the time of pulse data detection (conventional art).

FIG. 11 is a flowchart of an example of the method of judging an appropriate set value of the protrusion amount of the blood-flow-suppressing projection 21 applied to the present specific example. FIG. 12A, FIG. 125, FIG. 13A, FIG. 135, FIG. 14A and FIG. 14B are diagrams each depicting an example of measurement data obtained by the pulse data detecting method and analysis data obtained by frequency analysis, according to the present specific example. Here. FIG. 12A and FIG. 12B depict measurement data (pulse wave data based on the output from the light-receiving element) with a sufficiently high S/N ratio of pulse components and in a favorable measurement state and, analysis data obtained by frequency analysis thereof, respectively. FIG. 13A and FIG. 13B depict measurement data (pulse wave data based on the output from the light-receiving element) which prevents an S/N ratio of pulse components from being sufficiently ensured because of mixed noise due to, for example, ambient light and a motion of the human body causes a small signal amplitude, and analysis data obtained by frequency analysis thereof, respectively. FIG. 14A and FIG. 14B depict measurement data (pulse wave data based on the output from the light-receiving element) which affects to the extent that pulse components cannot be judged because of mixed significant noise due to, for example, a motion of the human body such as waving the hand or arm, and analysis data obtained by frequency analysis thereof, respectively. In FIG. 12A, FIG. 13A and FIG. 14A, the horizontal axis represents index values each indicating a measurement time (a value obtained by converting elapsed time based on a specific index), and the vertical axis represents measurement voltage values. An output from the light-receiving element 15 is not limited to a voltage of an output signal (a measurement voltage value) but may be another measurement value such as a current. Also, in FIG. 12B, FIG. 13B and FIG. 14B, the horizontal axis represents index values each representing a frequency component (a value obtained by converting each frequency based on a specific index), and the vertical axis represents index values each representing magnitudes of signal components in each frequency (a value obtained by converting light reception intensity at each frequency based on a specific index)

That is, at Step S200 according to the present first scheme, by following the flowchart depicted in FIG. 11, the CPU 11 first reads out the set value A stored in the memory 12 at Step S212. Next at Step S214, for the output value (sensor data) with the set value A, the CPU 11 calculates distribution data of light reception intensity for each frequency component by Fourier transform. The CPU 11 stores the calculated distribution data of light reception intensity for each frequency component in a predetermined storage area of the memory 12.

Here, the calculated distribution data of light reception intensity for each frequency component is specifically described. Here, for convenience of description, actual measurement data with a sufficiently high S/N ratio of pulse components included in the obtained measurement data and in a favorable measurement state is used for description. The measurement data with the specific set value A stored in the memory 12 is represented, for example, as in FIG. 12A. In FIG. 12A, regularly-repeated small waveforms PA each represent one pulse. In pulses of a person in a resting state, the pitch (time width) of one waveform is approximately equal to one second in general. Also, in the drawing, a large change (a dotted arrow in the drawing) PB of the measurement data formed of continuation of the small waveforms PA indicating pulses is due to a motion of the human body during measurement or the like. Also, the distribution data of light reception intensity for each frequency component obtained by Fourier transform of the measurement data depicted in FIG. 12A is represented, for example, as in FIG. 12B.

Next at Step S216, in the distribution data of light reception intensity for each frequency component, the CPU 11 extracts frequency components indicating peak values (maximum values) and its integer m-fold components (=2, 3, 4, . . . ) as pulse components. That is, as depicted in FIG. 12B, in the distribution data obtained by Fourier transform, the result is obtained such that, for example, a peak XA with an extremely-high, maximum light reception intensity (index value) appears at a frequency position of approximately 1 Hz (an index value of approximately 42 on the horizontal axis) and peaks XB, XC, XD, . . . each with a light reception intensity sufficiently lower than that of the peak XA appear at positions that are approximately integer multiples of the frequency of the peak XA. Here, the peak XA is a component corresponding to a pulse, and the peaks XB, XC, XD, . . . are components (non-abnormal values) corresponding to second, third-order, fourth-order, . . . , harmonics of the peak XA. Therefore, when noise components are hardly mixed in the obtained measurement data, the S/N ratio of the pulse components is sufficiently high, and the measurement state is favorable, the component corresponding to the peak XA due to pulses or components corresponding to the peaks XA, XB, XC, XD, . . . are extracted and removed from the distribution data as pulse components, whereby only the noise components included in the measurement data can be extracted.

Next at Step S218, the CPU 11 judges whether the intensity of the data obtained by excluding the pulse components extracted at Step S216 described above (that is, noise components) from the distribution data obtained by Fourier transform is equal or larger than a certain value (threshold) set in advance. At Step S218, when the intensity of the noise components is equal to or larger than the certain value (YES at Step S215), the CPU 11 judges and excludes the set value A at this moment as inappropriate (not being an appropriate set value), and performs processing at Step S226 onward, which will be described further below.

For example, when the signal amplitude of the measurement data is small and a sufficient S/N ratio cannot be ensured as depicted in FIG. 13A and FIG. 13B or when noise mixture is significant and pulse components cannot be distinguished as depicted in FIG. 14A and FIG. 14B, the CPU 11 judges the set value A at this moment as inappropriate.

Specifically, in the measurement data depicted in FIG. 13A, noises are slightly included in pulse waveforms DA as a whole. Also, the signal amplitude of each waveform is very small compared with the measurement data depicted in FIG. 12A described above. Furthermore, entire change tendencies of the measurement data are also influenced by low-frequency noises. On the other hand, in the measurement data depicted in FIG. 14A, measurement data DB on a front half (a left half of the drawing) has very large noise mixed therein, and pulse waveforms can hardly be distinguished. Still further, in measurement data DC on a latter half (a right half of the drawing), mixture of large noise is solved. However, noises are slightly included in pulse waveforms, and the signal amplitude of each waveform is very small compared with the measurement data depicted in FIG. 12A described above.

In the distribution data of light reception intensity for each frequency component obtained by Fourier transform of the measurement data, as depicted in FIG. 13B and FIG. 14B, peak components SA to some extent near a frequency corresponding to the pulses can be detected. However, compared with the analysis data depicted in FIG. 12A described above, there are many unstable factors (such as mixture of a plurality of peaks and the presence of a nearby noise component SB). Therefore, it is difficult to specify a frequency corresponding to the pulse from the peak components SA. Moreover, it is also difficult to distinguish harmonic components of pulse components due to mixture of noise components SC.

Therefore, when the signal amplitude of the measurement data is small and a sufficient S/N ratio cannot be ensured or when noise mixture is significant and pulse components cannot be distinguished, pulse components cannot be removed from the distribution data. Or, even if pulse components can be removed from the distribution data, the intensity of the noise components is relatively strong and is equal to or larger than a certain value (threshold). Accordingly, the CPU 11 judges the set value A set at this moment as inappropriate. Here, by taking one third of the light reception intensity in the frequency component indicating the peak value (maximum value) as a threshold, when the intensity of the data obtained by excluding the pulse components from the distribution data exceeds this threshold, the CPU 11 judges that noise is mixed in each frequency component to the extent that pulse components cannot be distinguished.

On the other hand, when the intensity of the noise components is weaker than the certain value (threshold) (NO at Step S218), the CPU 11 judges at Step S222 whether the light reception intensity in the frequency component indicating the peak value (maximum value) is maximum in the protrusion amounts of the blood-flow-suppressing projection 21 so far. That is, the CPU 11 judges whether the light reception intensity in the frequency component of the peak XA corresponding to the pulse depicted in FIG. 12B is maximum among the light reception intensities of peaks corresponding to the pulses extracted from the set values A (protrusion amounts of the blood-flow-suppressing projection 21) set in the measurements so far.

Then at Step S222, when the light reception intensity in the frequency component indicating the peak value is maximum among the light reception intensities in the protrusion amounts so far (YES at Step S222), the CPU 11 judges that the set value A at this moment is appropriate (an appropriate set value) and sets this set value as one of appropriate set value candidates at Step S224, and performs processing at Step S226 onward, which will be described further below. That is, when the light reception intensity in the frequency component of the peak XA is maximum of all measurements so far, the CPU 11 sets the set value A at this moment as one of appropriate set value candidates, associates this set value with the light reception intensity at the peak XA, and temporarily stores the resultant data in a predetermined storage area of the memory 12. As such, the processing at Step S218 and Step S222 substantially corresponds to processing of judging whether pulse data is appropriate based on the S/N ratio.

On the other hand, at Step S222, when the light reception intensity in the frequency component of the peak value is not maximum (NO at Step S222), the CPU 11 increments the set value A by 1 (A+1→A) at Step S226. The incremented set value A is temporarily stored in, for example, the memory 12. Then at Step S228, when the set value A is not larger than the maximum value N, the CPU 11 returns to Step S212, repeating the series of processing to which the above-described frequency analyses scheme by Fourier transform is applied (the method of judging an appropriate set value of the blood-flow-suppressing projection 21). By repeatedly performing the series of processing for each set value A, the latest and most appropriate set value candidate is stored in the memory 12 for update.

When the set value A is larger than the maximum value N at Step S228, the CPU 11 registers the latest (current) appropriate set value A candidate stored in the memory 12 as an appropriate set value at Step S230, and stores the set value in a predetermined storage area of the memory 12.

That is, by the processing of judging an appropriate set value of the protrusion amount of the blood-flow-suppressing projection 21 at Step S200 to which the above-described first scheme is applied, among the set values A from which measurement data and analysis data with a high S/N ratio and in a favorable measurement state can be obtained, a set value A with the highest S/N ratio is judged and registered as the most appropriate set value as depicted in FIG. 12A and FIG. 12B, for example. On the other hand, for example, as depicted in FIG. 13A, FIG. 13B, FIG. 14A and FIG. 14B, measurement data with a low S/N ratio and in a measurement state with a significant noise influence is excluded.

Next at Step S164, the CPU 11 determines the set value A of the blood-flow-suppressing projection 21 judged as an appropriate output at Step S200 described above, and performs computation processing on the output value (sensor data) from the light-receiving element 15 with respect to the determined set value A. Furthermore, at Step S168, the pulse rate calculating section 18 calculates a pulse rate. Here, at Step S130, the CPU 11 judges whether an error is present in the pulse rate calculation processing (or whether the calculated pulse rate is adequate). When an error is present in the pulse rate calculation processing (YES at Step S130), the CPU 11 judges that the set value of the blood-flow-suppressing projection 21 currently set is not appropriate, and returns to Step S140, repeating the above-described series of processing of judging an appropriate set value (Step S140 to Step S164). On the other hand, when an error is not present in the pulse rate calculation processing (NO at Step S130), the CPU 11 outputs the calculated pulse rate to the display section 19 at Step S170. Next at Step S172, the display section 19 displays the calculated pulse rate as pulse data. The calculated pulse rate is also associated with the set value A (protrusion amount) at that moment and time data at the time of measurement, etc., and is stored in a predetermined storage area of the memory 12.

Next at Step S174, the CPU 11 judges whether an end instruction is provided to the operating section 10 from the user. When an end instruction is not provided (NO at Step S174), the CPU 11 returns to Step S166, repeating the above-described processing of calculating a pulse rate. On the other hand, when an end instruction is provided from the user (YES at Step S174), the CPU 11 performs predetermined end processing (such as storing the pulse rate and discarding measurement data) at Step S176, and then ends the processing.

As such, in the present specific example, by controlling the protrusion amount of the blood-flow-suppressing projection 21 placed on the downstream side of the measurement region in a stepwise manner to purposely change a force for pressing or compressing the blood vessel in a stepwise manner, an appropriate set value of the protrusion amount of the blood-flow-suppressing projection 21 from which an output with a favorable S/N ratio can be obtained from the light-receiving element 15 is determined. As a result, according to the present specific example, an appropriate output level can be obtained regardless of the state of placement of the pulse data detecting apparatus 1 on the human body, and whereby stable and reliable pulse measurement can be performed.

Also in the present specific example, the set value registered (stored) in advance, that is, for example, the appropriate set value of the protrusion amount of the blood-flow-suppressing projection 21 determined in the previous measurement and registered is set as a default value or an initial value in the next pulse measurement onward. As a result, according to the present specific example, pulse measurement can be performed by using the set value registered in advance until the obtained measurement data is judged as inappropriate. Therefore, processing for determining a user-friendly measuring apparatus with reduced process load and expeditious measurement processing can be provided.

In the present specific example, the case is described where a frequency analysis scheme by Fourier transform is applied as a method of judging an appropriate set value of the protrusion amount of the blood-flow-suppressing projection 21. However, the present invention is not limited thereto. That is, in the present invention, another scheme other than Fourier transform may be applied as long as frequency analysis is applied to judge the quality of an output signal (for example, an S/N ratio) from the light-receiving element 15.

(Second Scheme)

Next, another example of scheme applicable to Step S200 in the above-described specific example is described.

FIG. 15 is a flowchart of another example of the method of judging an appropriate set value of the protrusion amount of the blood-flow-suppressing projection 21 applied to the present specific example. Here, description is made by referring to the processing procedure of the above-described specific example (the flowchart depicted in FIG. 10) and the measurement data obtained in the processing procedure (pulse wave data based on the output from the light-receiving element depicted in FIG. 12A, FIG. 13A and FIG. 14A).

In the method of judging an appropriate set value of the protrusion amount of the blood-flow-suppressing, projection 21, in the above-described first scheme, the case is described where the measurement data is subjected to Fourier transform and, based on its analysis data, processing of judging an appropriate set value is performed. In the present second scheme, processing of judging an appropriate set value is performed based on a time of the output value (sensor data) in the measurement data and a change amount of light reception intensity.

That is, at Step S200 according to the second scheme applied to the above-described specific example (the flowchart depicted in FIG. 10), the CPU 11 performs processing according to the flowchart depicted in FIG. 15. First at Step S262, the CPU 11 reads out the set value A stored in the memory 12. Next at Step S264, the CPU 11 extracts from measurement data (pulse wave data) for a predetermined time a time (X) and a light reception intensity (Y) of a peak value of each waveform (refer to the waveforms PA in FIG. 12A) that increases and decreases. Here, the peak value of each waveform is found by, for example, differentiating the light reception intensity (Y) with respect to the time (X). The CPU 11 associates the time (X) and the light reception intensity (Y) of the peak value of each waveform, and temporarily stores the result in the memory 12 in the form of (X1, Y1), (X2, Y2), (X3, Y3), . . . .

Next at Step S266, the CPU 11 calculates a difference $\Delta X_p = X_{p+1} - X_p$ (p=1, 2, 3, . . . ) between the times (X) of the peak values of adjacent waveforms and a difference $\Delta Y_p = Y_{p+1} - Y_p$ (p=1, 2, 3, . . . ) between the light reception intensities (Y) of these waveforms, and temporarily stores the result in the memory 12 as difference data. Here, the difference $\Delta X_p$ in time (X) of the peak values corresponds to a pitch between adjacent waveforms, and the difference $\Delta Y_p$ in light reception intensity (Y) corresponds to an amplitude of each waveform. The difference $\Delta X_p$ in time (X) of the peak values is not limited to the one using peak values of waveforms as long as the difference is to derive a time corresponding to a pitch between waveforms Next at Step S268, the CPU 11 judges whether a change amount (or dispersion) of each difference $\Delta X_p$ in time (X) of the peak values calculated for adjacent waveforms at Step S266 is larger than a certain value set in advance (threshold). When the change amount of each difference $\Delta X_p$ is larger than the certain value (YES at Step S268), the CPU 11 judges at Step S274 that the set value A at this moment is inappropriate (is not an appropriate set value) and excludes the set value A, and then performs processing at Step S280 onward, which will be described further below.

For example, when very large noise is mixed and pulse waveforms can be hardly distinguished as depicted in the measurement data DB of FIG. 14A, each difference $\Delta X_p$ in time (X) of the peak values of adjacent waveforms may be large. Also, when noises are slightly included in pulse waveforms as depicted in the waveforms DA of FIG. 13A and the measurement data DC of FIG. 14A, each difference $\Delta X_p$ in time (X) of the peak values of waveforms may be small irregularly. Thus, in order to exclude the measurement data in a measurement state as described above, the CPU 11 judges the set value A at this moment as inappropriate.

On the other hand, at Step S268, when the change amount of each difference $\Delta X_p$ in time (X) of the peak values of waveforms is not larger than the certain value (NO at Step S268), the CPU 11 judges at Step S270 whether the change amount (or dispersion) of each difference $\Delta Y_p$ in light reception intensity (Y) of adjacent waveforms is larger than a certain value set in advance (threshold). When the change amount of each difference $\Delta Y_p$ is larger than the certain value (YES at Step S270), the CPU 11 judges at Step S274 that the set value A at this moment is inappropriate and excludes the set value A, and then performs processing at Step S280 onward, which will be described further below.

For example, when very large noise is mixed and the amplitude of each waveform is greatly changed as depicted in the measurement data DB of FIG. 14A, the change amount of each difference $\Delta Y_p$ in light reception intensity (Y) of adjacent waveforms is large. Therefore, in order to exclude the measurement data in a measurement state as described above, the CPU 11 judges the set value A at this moment as inappropriate.

On the other hand, at Step S270, when the change amount of each difference $\Delta Y_p$ in light reception intensity (Y) of waveforms is not larger than the certain value (NO at Step S270), the CPU judges at Step S272 whether each difference $\Delta Y_p$ in light reception intensity (Y) of waveforms is extremely smaller than a certain value (threshold) set in advance (that is, too small) When each difference $\Delta Y_p$ in light reception intensity (Y) is too small (YES at Step S272), the CPU 11 judges at Step S274 the set value A at this moment as inappropriate and excludes the set value A, and then performs processing at Step S280 onward, which will be described further below.

For example, when the output signal from the light-receiving element 15 is weak (the measurement voltage is low) and the amplitude of each waveform is very small as depicted in the waveform DA of FIG. 13A, the difference $\Delta Y_p$ in light reception intensity (Y) of adjacent waveforms is extremely small. Therefore, in order to exclude the measurement data in a measurement state as described above, the CPU 11 judges the set value A at this moment as inappropriate On the other hand, when the difference $\Delta Y_p$ in light reception intensity (Y) is not too small (NO at step S272), the CPU 11 judges at Step S276 whether an average value of the differences $\Delta Y_p$ in light reception intensity (Y) in the measurement data is maximum among average values of differences $\Delta Y_p$ in respective set values A (protrusion amounts of the blood-flow-suppressing projection 21) set in the measurements so far.

Then at Step S276, when the average value of the differences $\Delta Y_p$ in light reception intensity (Y) is maximum among average values of the differences $\Delta Y_p$ in the protrusion amounts so far (YES at Step 276), the CPU 11 judges at Step S278 that the set value A at this moment is appropriate (an appropriate set value) and sets this set value as one of appropriate set value candidates, and then performs processing at Step S280 onward, which will be described further below, That is, when the average value of the differences $\Delta Y_p$ in light reception intensity (Y) is maximum among the measurements so far, the CPU 11 sets the set value A at this moment as one of appropriate set value candidates, associates the candidate with the average value of the differences $\Delta Y_p$ in light reception intensity (Y), and temporarily stores the result in a predetermined storage area of the memory 12.

On the other hand, at Step S276, when the average value of the differences $\Delta Y_p$ in light reception intensity (Y) is not maximum (NO at Step S276), the CPU 11 increments the set value A by 1 (A+1→A) at Step S280. The incremented set value A is temporarily stored in, for example, the memory 12. Then, at Step S282, when the set value A is not larger than the maximum value N, the CPU 11 returns to Step S262 and, for the incremented set value A, repeats the above-described series of processing (the method of judging an appropriate set value of the blood-flow-suppressing projection 21) to which the analysis scheme based on the difference $\Delta X_p$ in time (X) of the peak values of adjacent waveforms and the difference $\Delta Y_p$ in light reception intensity (Y) of the waveforms is applied. By repeating this series of processing for each set value A, a latest and most appropriate set value candidate is stored in the memory 12 for update.

At Step S282, when the set value A is larger than the maximum value N, as with the above-described first scheme, the CPU 11 registers, at Step S230, the latest (current) appropriate set value A candidate stored in the memory 12 as the most appropriate set value, and stores the set value A in a predetermined storage area of the memory 12. Thereafter, the processing at Step S164 onward is performed in the flowchart of FIG. 10.

That is, by the processing of judging an appropriate set value of the protrusion amount of the blood-flow-suppressing projection 21 at Step S200 to which the above-described second scheme is applied, a set value A with the largest amplitude average value is judged and registered as the most appropriate set value, among the set values A from which measurement data can be obtained where the pulse waveform pitch and amplitude are uniform and the amplitude is sufficiently large as depicted in, for example, FIG. 12A. On the other hand, measurement data where the waveform pitch and amplitude are not uniform due to noise mixture and measurement data with a very small amplitude as depicted in, for example, FIG. 13A and FIG. 14A, are excluded. In the judgment processing using the difference $\Delta X_p$ in time (X) of the peak values of waveforms and the difference $\Delta Y_p$ in light reception intensity (Y) thereof at Step S268, S270, and S272 described above, the CPU 11 applies as thresholds, for example, a pulse waveform pitch and amplitude obtained by measuring a pulse for a predetermined period.

As has been described above, according to the present specific example, by controlling the protrusion amount of the blood-flow-suppressing projection 21 placed on the downstream side of the measurement region in a stepwise manner to purposely change a force for pressing or compressing the blood vessel in a stepwise manner, an appropriate set value of the protrusion amount of the blood-flow-suppressing projection 21 from which an output with a favorable pulse wave pitch and amplitude can be obtained from the light-receiving element 15 is determined. As a result according to the present specific example, an appropriate output level can be obtained regardless of the state of placement of the pulse data detecting apparatus 1 on the human body, and thereby stable and reliable pulse measurement can be performed.

Also in the present specific example, by computation processing of performing calculation of the difference $\Delta X_p$ in time (X) of peak values of adjacent waveforms included in measurement data and the difference $\Delta Y_p$ in light reception intensity (Y) thereof and making comparison between each calculated difference and a certain value (threshold), an appropriate set value of the protrusion amount of the blood-flow-suppressing projection is judged. As a result, according to the present specific example, the processing of determining an appropriate set value of the protrusion amount of the blood-flow-suppressing projection 21 can be performed by simple computation processing, a user-friendly measuring apparatus with reduced process load and expeditious measurement processing can be provided. Here, in the present second scheme, an appropriate set value of the protrusion amount of the blood-flow-suppressing projection can be judged basically as long as measurement data including waveforms of at least two pulses is present. In actual pulse measurement, measurement data including several to several tens of waveforms is preferable. In this case, an operation of measuring and capturing an output from the light-receiving element 15 is performed at a time of, for example, in the order of several to several tens of seconds.

While the present invention has been described with reference to the preferred embodiments, it is intended that the invention be not limited by any of the details of the description therein but includes all the embodiments which fall within the scope of the appended claims.

What is claimed is:

1. A pulse data detecting apparatus comprising:
a projection configured to suppress blood flow in a blood vessel to increase a blood pressure of a measurement region, the projection being configured to press or compress a body surface and to be settable at a plurality of protrusion amounts;
a sensor configured to detect a plurality of pieces of pulse data, each of the plurality of pieces of pulse data being detected in a state in which the projection is set at a respective one of the plurality of protrusion amounts and indicating a pulse intensity at a time at which the sensor is in contact with the body surface;
an output device configured to output one of the plurality of pieces of pulse data detected by the sensor;
a memory configured to store, as an output-time protrusion amount, a protrusion amount of the projection at a time at which the one of the plurality of pieces of pulse data is outputted; and
a processor which executes a stored program to perform functions comprising:
(i) when the output-time protrusion amount is stored in the memory, setting the projection at the output-time protrusion amount stored in the memory, and outputting a piece of pulse data detected by the sensor with the projection set at the output-time protrusion amount; and
(ii) when the output-time protrusion amount is not stored in the memory:
(a) sequentially changing the protrusion amount of the projection to each of the plurality of protrusion amounts;
(b) for each one of the protrusion amounts to which the projection is sequentially changed:
in a state in which the blood flow in the blood vessel is suppressed by the projection, storing a piece of pulse data detected by the sensor in association with the one of the plurality of protrusion amounts to which the projection has been changed; and
calculating, by Fourier transform, intensity distribution data of the pulse intensity for the stored piece of pulse data, the intensity distribution data including the pulse intensity at each of a plurality of frequency components, and the intensity distribution data including a maximum value corresponding to a frequency component at which the pulse intensity is highest;
(c) identifying a highest maximum value among the maximum values obtained from the intensity distribution data corresponding to each of the plurality of protrusion amounts; and
(d) storing, in the memory, a protrusion amount associated with the identified highest maximum value, as the output-time protrusion amount,
wherein the pulse intensity indicates an intensity of a measurement value of a voltage detected according to time by the sensor.

2. The pulse data detecting apparatus according to claim 1, wherein the projection is arranged on a downstream side of the blood flow with respect to a position at which the sensor is placed, and is configured to suppress the blood flow on the downstream side by pressing or compressing the body surface.

3. The pulse data detecting apparatus according to claim 1, wherein the projection is structured to protrude in a skin direction by filling a bag-shaped member with a fluid to increase a volume thereof.

4. The pulse data detecting apparatus according to claim 1, wherein the projection is structured to protrude by moving a stick-shaped member in a skin direction.

5. The pulse data detecting apparatus according to claim 1, wherein the projection is structured to protrude in a skin direction by rotating a flat member.

6. The pulse data detecting apparatus according to claim 1, wherein the projection is configured to press or compress the body surface intermittently with a detection timing of the sensor so as to prevent a compressed state from continuing for a predetermined time.

7. A method of detecting pulse data using a pulse data detecting apparatus, the pulse data detecting apparatus including (i) a projection configured to suppress blood flow in a blood vessel to increase a blood pressure of a measurement region, the projection being configured to press or compress a body surface and to be settable at a plurality of protrusion amounts, (ii) a sensor configured to detect a plurality of pieces of pulse data, each of the plurality of pieces of pulse data being detected in a state in which the projection is set at a respective one of the plurality of protrusion amounts and indicating a pulse intensity at a time at which the sensor is in contact with the body surface, (iii) an output device configured to output one of the plurality of pieces of pulse data detected by the sensor, and (iv) a memory configured to store, as an output-time protrusion amount, a protrusion amount of the projection at a time at which the one of the plurality of pieces of pulse data is outputted, and the method comprising:
when the output-time protrusion amount is stored in the memory, setting the projection at the output-time protrusion amount stored in the memory, and outputting a piece of pulse data detected by the sensor with the projection set at the output-time protrusion amount; and
when the output-time protrusion amount is not stored in the memory:
(a) sequentially changing the protrusion amount of the projection to each of the plurality of protrusion amounts;
(b) for each one of the protrusion amounts to which the projection is sequentially changed:
in a state in which the blood flow in the blood vessel is suppressed by the projection, storing a piece of pulse data detected by the sensor in association with the one of the plurality of protrusion amounts to which the projection has been changed; and
calculating, by Fourier transform, intensity distribution data of the pulse intensity for the stored piece of pulse data, the intensity distribution data including the pulse intensity at each of a plurality of frequency components, and the intensity distribution data including a maximum value corresponding to a frequency component at which the pulse intensity is highest;

(c) identifying a highest maximum value among the maximum values obtained from the intensity distribution data corresponding to each of the plurality of protrusion amounts; and (d) storing, in the memory, a protrusion amount associated with the identified highest maximum value, as the output-time protrusion amount, wherein the pulse intensity indicates an intensity of a measurement value of a voltage detected according to time by the sensor.

8. The method according to claim 7, wherein the projection is arranged on a downstream side of the blood flow with respect to a position at which the sensor is placed, and is configured to suppress the blood flow on the downstream side by pressing or compressing the body surface.

9. The method according to claim 7, wherein the projection is structured to protrude in a skin direction by filling a bag-shaped member with a fluid to increase a volume thereof.

10. The method according to claim 7, wherein the projection is structured to protrude by moving a stick-shaped member in a skin direction.

11. The method according to claim 7, wherein the projection is structured to protrude in a skin direction by rotating a flat member.

12. The method according to claim 7, wherein the projection is configured to press or compress the body surface intermittently with a detection timing of the sensor so as to prevent a compressed state from continuing for a predetermined time.

13. A non-transitory computer-readable storage medium having stored thereon a pulse data detection program that is executable by a computer of a pulse data detecting apparatus, the pulse data detecting apparatus further including (i) a projection configured to suppress blood flow in a blood vessel to increase a blood pressure of a measurement region, the projection being configured to press or compress a body surface and to be settable at a plurality of protrusion amounts, (ii) a sensor configured to detect a plurality of pieces of pulse data, each of the plurality of pieces of pulse data being detected in a state in which the projection is set at a respective one of the plurality of protrusion amounts and indicating a pulse intensity at a time at which the sensor is in contact with the body surface, (iii) an output device configured to output one of the plurality of pieces of pulse data detected by the sensor, and (iv) a memory configured to store, as an output-time protrusion amount, a protrusion amount of the projection at a time at which the one of the plurality of pieces of pulse data is outputted, and the program being executable to control the computer to perform functions comprising:

when the output-time protrusion amount is stored in the memory, setting the projection at the output-time protrusion amount stored in the memory, and outputting a piece of pulse data detected by the sensor with the projection set at the output-time protrusion amount; and when the output-time protrusion amount is not stored in the memory:

(a) sequentially changing the protrusion amount of the projection to each of the plurality of protrusion amounts;

(b) for each one of the protrusion amounts to which the projection is sequentially changed:

in a state in which the blood flow in the blood vessel is suppressed by the projection, storing a piece of pulse data detected by the sensor in association with the one of the plurality of protrusion amounts to which the projection has been changed; and calculating, by Fourier transform, intensity distribution data of the pulse intensity for the stored piece of pulse data, the intensity distribution data including the pulse intensity at each of a plurality of frequency components, and the intensity distribution data including a maximum value corresponding to a frequency component at which the pulse intensity is highest;

(c) identifying a highest maximum value among the maximum values obtained from the intensity distribution data corresponding to each of the plurality of protrusion amounts; and (d) storing, in the memory, a protrusion amount associated with the identified highest maximum value, as the output-time protrusion amount, wherein the pulse intensity indicates an intensity of a measurement value of a voltage detected according to time by the sensor.

14. The non-transitory computer-readable storage medium according to claim 13, wherein the projection is arranged on a downstream side of the blood flow with respect to a position at which the sensor is placed, and is configured to suppress the blood flow on the downstream side by pressing or compressing the body surface.

15. The non-transitory computer-readable storage medium according to claim 13, wherein the projection is structured to protrude in a skin direction by filling a bag-shaped member with a fluid to increase a volume thereof.

16. The non-transitory computer-readable storage medium according to claim 13, wherein the projection is structured to protrude by moving a stick-shaped member in a skin direction.

17. The non-transitory computer-readable storage medium according to claim 13, wherein the projection is structured to protrude in a skin direction by rotating a flat member.

18. The non-transitory computer-readable storage medium according to claim 13, wherein the projection is configured to press or compress the body surface intermittently with a detection timing of the sensor so as to prevent a compressed state from continuing for a predetermined time.

* * * * *